(12) United States Patent
Raleigh

(10) Patent No.: US 8,774,903 B2
(45) Date of Patent: Jul. 8, 2014

(54) MEDICAL IMAGING APPARATUS AND METHOD

(75) Inventor: Gregory G. Raleigh, Woodside, CA (US)

(73) Assignee: Headwater Partners II LLC, Redwood City, CA (US)

(*) Notice: Subject to any disclaimer, the term of this patent is extended or adjusted under 35 U.S.C. 154(b) by 167 days.

(21) Appl. No.: 13/074,003

(22) Filed: Mar. 28, 2011

(65) Prior Publication Data

US 2011/0237940 A1 Sep. 29, 2011

Related U.S. Application Data

(60) Provisional application No. 61/317,794, filed on Mar. 26, 2010, provisional application No. 61/317,797, filed on Mar. 26, 2010.

(51) Int. Cl.
| | | |
|---|---|---|
| *A61B 6/00* | (2006.01) | |
| *A61B 8/00* | (2006.01) | |
| *A61B 1/00* | (2006.01) | |
| *A61F 2/24* | (2006.01) | |
| *A61B 8/12* | (2006.01) | |
| *A61F 2/958* | (2013.01) | |
| *A61B 8/08* | (2006.01) | |
| *A61B 19/00* | (2006.01) | |
| *A61M 25/10* | (2013.01) | |
| *A61B 17/32* | (2006.01) | |

(52) U.S. Cl.
CPC ........... *A61B 1/00177* (2013.01); *A61B 8/0883* (2013.01); *A61B 8/4444* (2013.01); *A61B 8/5238* (2013.01); *A61B 2019/5278* (2013.01); *A61F 2/2433* (2013.01); *A61B 8/12* (2013.01); *A61B 8/4477* (2013.01); *A61B 1/00181* (2013.01); *A61M 25/104* (2013.01); *A61B 8/445* (2013.01); *A61M 25/10* (2013.01); *A61F 2/958* (2013.01); *A61B 17/32002* (2013.01)
USPC .......... 600/476; 600/473; 600/478; 600/459; 600/462

(58) Field of Classification Search
USPC ................................ 600/407–429, 437–480
See application file for complete search history.

(56) References Cited

U.S. PATENT DOCUMENTS

| | | | | |
|---|---|---|---|---|
| 5,797,849 | A * | 8/1998 | Vesely et al. | 600/461 |
| 6,246,898 | B1 * | 6/2001 | Vesely et al. | 600/424 |
| 2008/0009746 | A1 | 1/2008 | Forster et al. | |
| 2009/0005679 | A1 * | 1/2009 | Dala-Krishna | 600/437 |
| 2009/0131798 | A1 * | 5/2009 | Minar et al. | 600/463 |
| 2010/0210945 | A1 * | 8/2010 | Zhang | 600/443 |
| 2010/0217119 | A1 | 8/2010 | Forster et al. | |

* cited by examiner

*Primary Examiner* — Sanjay Cattungal
(74) *Attorney, Agent, or Firm* — Kilpatrick Townsend & Stockton LLP

(57) ABSTRACT

A medical device is used to image a body cavity using a plurality of axially and angularly spaced imaging sensors. Each imaging sensor generates an image that is distinct from one another due to distinct fields of vision. Each image includes an overlapping zone with commonalities that are used to extrapolate a greater calibrated image.

66 Claims, 17 Drawing Sheets

502

504 illuminator   Camera
  Stent     System
              Blood Vessel 506      lens
Angioplastic
Balloon

508

510

614

MEDICAL IMAGING APPARATUS AND METHOD

CROSS-REFERENCES TO RELATED APPLICATIONS

This application claims the benefit of U.S. Provisional Application No. 61/317,794, filed on Mar. 26, 2010, and U.S. Provisional Application No. 61/317,797, filed on Mar. 26, 2010, and the entirety of each are incorporated by reference herein.

BACKGROUND

Minimum invasive surgery such as arthroscopy, balloon angioplasty, and vascular stenting, has revolutionized human medicine in the past few decades. In contrast to the traditional surgical method where large incisions are made and patients are examined and operated in an "open" manner, minimum invasive surgery only requires small incisions, surgery and diagnosis are carried out remotely with the aid of miniature cameras placed at the surgical sites. The ability to accurately image the surgical site is therefore crucial to the success of minimum invasive surgery and diagnosis and an improved imaging capability has the potential to further improve minimum invasive surgery and diagnosis.

Prior methods and devices included the use of catheters requiring movement and/or moving parts to direct imaging energy, such as ultrasonic energy, to generate images. Often, such an image is a highly distorted image, which requires a great deal of experience to interpolate. During imaging, the operator is typically required to directionally manipulate a catheter like device in various directions within a body cavity to obtain an image. The operator must take great care during this procedure so as to not miss any relevant features of the body cavity during imaging. Accordingly, using such devices requires great skill and experience to use.

BRIEF SUMMARY

Some embodiments of the invention relate to a method having aspects where a first cavity portion of a greater body cavity is imaged using a first imaging sensor of a catheter to generate a first image. A second cavity portion of the greater body cavity is imaged using a second imaging sensor of the catheter to generate a second image. The first and second cavity portions are contiguous portions of the greater body cavity.

In further aspects of this method, the first and second images partially overlap in an overlap portion, and a greater image of the greater body cavity is generated from at least the first and second images by calibrating the overlap portion.

In yet further aspects of the method, generating the greater image includes identifying common features of each of the first and second images in the overlap portion and adjusting at least one of the first and second images according to the common features.

In yet further aspects of the method, the first and second images are pixilated and the common features comprise pixels.

In yet further aspects of the method, the position of the catheter in the body cavity is maintained when imaging the first and second cavity portions.

In yet further aspects of the method, during imaging the first cavity portion, the first cavity portion is partially out of operational range of the second imaging sensor, and during imaging the second cavity portion, the second cavity portion is partially out of operational range of the first imaging sensor.

In yet further aspects of the method, the first and second imaging sensor are axially and angularly displaced from one another.

Another embodiment of the invention relates to a method having aspects where a device having a plurality of angularly and axially separated imaging sensors is inserted into a calibration target assembly having a plurality of calibration references. Each imaging sensor has a distinct field of view of at least one calibration reference of the plurality of calibration references. A plurality of images is generated of the calibration references using the plurality of imaging sensors. Imaging accuracy for the plurality of imaging sensors is determined based on dimensional aspects of the plurality of imaged calibration references. An imaging correction factor is determined for the catheter based on the determining imaging accuracy.

In further aspects of this method, a calibrated image is generated by applying the correction factor to a subsequent image generated by the device.

In yet further aspects of the method, the device includes a catheter having a balloon covering the plurality of imaging sensors, the balloon having a plurality of balloon imaging references in the fields of view of the plurality of imaging sensors.

In yet further aspects of the method, imaged calibration references are images of three-dimensional aspects corresponding to physical distortions of the balloon imaging references.

In yet further aspects of the method, calibration references are cavities and/or nodules on a surface of the calibration target assembly.

In yet further aspects of the method, the nodules have a different resiliency than that of the surface.

Another embodiment of the invention is related to a method having aspects where an interior portion of a balloon having distortable reference markings is imaged using a plurality of optical imaging sensors to produce a respective plurality of optical images. A calibrated image is generated from the plurality of optical images by calibrating imaged distortions of the reference markings with known dimensions of the reference markings.

Another embodiment of the invention is related to a method having aspects where an interior portion of a balloon having distortable reference markings is imaged using a plurality of ultrasound imaging sensors to produce a respective plurality of ultrasound images. A calibrated image is generated from the plurality of ultrasound images by calibrating imaged distortions of the reference markings with known dimensions of the reference markings.

In further aspects of this method, the balloon is of a catheter that is inserted into a body cavity.

In yet further aspects of the method, the body cavity is exposed with imaging energy using the catheter, the imaging energy comprising one of white light, infrared light, sonar, ultrasonic, or LIDAR energy.

In yet further aspects of the method, the catheter is used to place a stent in a portion of the body cavity corresponding to the calibrated image.

In yet further aspects of the method, generating the calibrated image further includes identifying partially-overlapping regions of the plurality of images.

In yet further aspects of the method, the imaged distortions of the reference markings are used to extrapolate three-dimensional features of a body cavity in contact with the balloon.

In yet further aspects of the method, the balloon is being pressurized within a portion of the body cavity having a first pliancy and a second pliancy, and generating the calibrated image includes calibrating imaged distortions of the reference markings over the first pliancy and imaged distortions of the reference markings over the second pliancy with known dimensions of the reference markings.

In yet further aspects of the method, the plurality of images are produced in accordance with changing balloon pressures, and the imaged distortions of the reference markings over the first pliancy show a greater or lesser rate of distortional change, over the changing balloon pressures, than the imaged distortions of the reference markings over the second pliancy. In the above and what follows, it should be understood that in many aspects of the invention the term "changing balloon fill volume" may be used in place of "changing balloon pressure".

In yet further aspects of the method, the balloon has an expandable covering that promotes expansion of the balloon in a radial dimension and application of a uniform outward force against the body cavity.

Another embodiment of the invention relates to an apparatus having aspects including an elongated catheter having a distal portion. A plurality of imaging sensors is coupled to the distal portion. The plurality of imaging sensors are axially and angularly spaced apart from one another. The plurality of imaging sensors have distinct and partially-overlapping fields of view with respect to one another.

In further aspects of the apparatus, a balloon is coupled to the distal portion and covering the plurality of imaging sensors.

In yet further aspects of the apparatus, the balloon has a plurality of distortable reference markings.

In yet further aspects of the apparatus, a reference marking pattern emitter is coupled to the distal portion.

In yet further aspects of the apparatus, the balloon includes an expandable covering having a mid-covering portion and end-covering portions, respectively covering a mid-portion and end-portions of the balloon, and the mid-covering portion has greater relative elasticity than the end-covering portions.

In yet further aspects of the apparatus, the imaging sensors include optical or piezoelectric devices.

In yet further aspects of the apparatus, each imaging sensor of the plurality of imaging sensors includes an imaging transmission device.

In yet further aspects of the apparatus, the imaging transmission device comprises at least one of a white light, infrared light, sonar, or ultrasonic emitter.

In yet further aspects of the apparatus, each imaging sensor of the plurality of imaging sensors includes a lens.

In yet further aspects of the apparatus, each imaging sensor of the plurality of imaging sensors comprises a CCD or APS imaging sensor.

In yet further aspects of the apparatus, the catheter includes a stent proximate to the balloon.

In yet further aspects of the apparatus, the stent is located over a stenting balloon on the catheter.

Another embodiment of the invention relates to a system having aspects that include an elongated catheter having a balloon coupled to a distal portion of the elongated catheter. A plurality of optical imaging sensors is coupled to the catheter within the balloon. The balloon has a plurality of distortable reference markings. An image processing device coupled to the elongated catheter, the image processing device including a processor coupled to memory having instructions executable by the processor to perform a method where an interior portion of the balloon is imaged using the plurality of optical imaging sensors to produce a respective plurality of optical images. A calibrated image is generated from the plurality of optical images by calibrating imaged distortions of the reference markings with known dimensions of the reference markings.

In yet further aspects of the system, a balloon inflation controller is coupled to a pressure source and the balloon. The balloon inflation controller is configured to regulate balloon pressure.

In yet further aspects of the system, the imaging processing device includes a camera system.

In yet further aspects of the system, the catheter includes at least one stent.

BRIEF DESCRIPTION OF THE DRAWINGS

Various embodiments of the invention are disclosed in the following detailed description and the accompanying drawings.

DETAILED DESCRIPTION

Figure 1A:
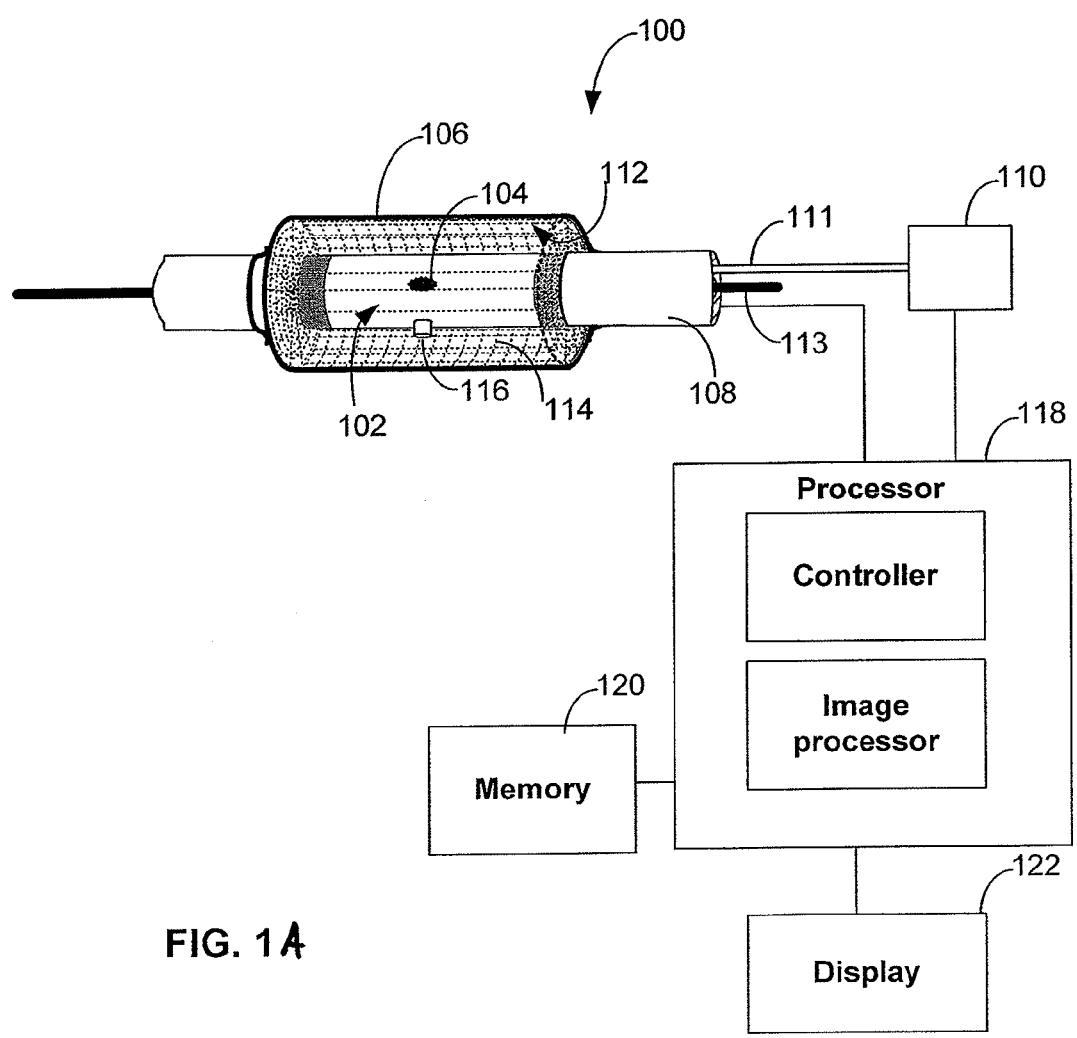
FIGS. 1A-1C are schematic diagrams illustrating aspects of an imaging system in accordance with some embodiments.

Embodiments of the invention are related to imaging methods and devices using a medical device such as a minimally invasive medical device, such as an arthroscopy device, a laparoscopy device, a cardiac catheter, or generally any medical device where remote imaging is used to guide the device. For example, a catheter can include an array of imaging sensors that are arranged in a pattern such that each imaging sensor has a distinct field of view, and accordingly image a portion of a body cavity, such as bodily lumen, that is distinct with respect to the other imaging sensors. The imaging sensors can be configured for use with energy transmitters used for imaging (e.g., piezoelectric transducer, LED), or alternatively incorporate the functionality of an energy transmitter (e.g., a piezoelectric transducer used to both transmit energy and receive reflected energy).

Each imaging sensor generally has a field of view that partially overlaps with at least one adjacent field of view. For example, five imaging sensors are angularly spaced apart from one another about a distal (i.e., working) end of a catheter. Furthering this example, each imaging sensor is angularly spaced apart by 72° to equally cover an entire diameter of the catheter. Each imaging sensor in this example has a field of view than 72° greater than field of view, for example 90°. Each field of view partially overlaps an adjacent field or fields of view. For example, each imaging sensor may overlap an adjacent imaging sensor by 18°, or overlap both adjacent fields of view by 9°. Accordingly, a plurality of images generated by the imaging sensors would include partially overlapping zones.

Common features in these zones can be used to calibrate each image with one another to create a greater image. Thus, in such a manner, directional movement of the catheter (to move an imaging sensor directly face a bodily feature) or incorporation of moving parts, is not required in some embodiments to image a desired bodily feature, since the device can be configured to capture a 360° image of a contiguous portion of body cavity. Accordingly, as long as the catheter is in the general vicinity of a feature, the feature will be imaged. Thus, the catheter requires a relatively low skill level for imaging, in comparison to directionally based devices of the prior art. However, it should be understood that a 360° arrangement of imaging sensors is an example and not a requirement. Generally, more than one imaging sensor is required, i.e., a first imaging sensor and a second imaging sensor, having at least one partially overlapping field of view for generating first and second images that partially overlap in an overlap portion, or a single imaging sensor which rotates to produce a plurality of overlapping images. The overlap portion will include common features that can be used to calibrate the images with one another.

In some embodiments, the catheter can include a reference apparatus, such as a balloon, that is used to interpolate proper dimensionality for images captured by the imaging sensors. Such references can include deformable reference markings (e.g., a grid pattern) on an interior surface of a balloon. In some embodiments, such an arrangement allows the balloon to be constructed from a material that is completely or partially opaque, since the deformation of the reference markings can be used to provide all the necessary imaging. Generally, when using optical imaging sensors a balloon is used to provide a clear field of view from the imaging sensor to a pressurized balloon wall in contact with a bodily feature, since blood or other fluids may otherwise block the view. However, it should be understood, that inclusion of the balloon is not a requirement, for example, when using sonar or ultrasonic imaging sensors.

In some embodiments, the catheter may be coupled to a video projection system for real time viewing by the operator and/or for remote viewing by others. As such, the video projection system will operate the catheter using a video stream of calibrated images for operational guidance.

Medical imaging using optical lenses are disclosed. For example, one embodiment includes an imaging system having a camera system placed inside an expandable covering (termed herein also as balloon covered imaging system), where the expandable covering includes reference markings that aid in imaging and characterization. In some embodiments, the expandable covering includes an expandable balloon. In some embodiments, the markings are drawn (e.g., printed) on a surface (e.g., interior surface) of the balloon. In some embodiments, the markings are projected onto a surface (e.g., interior surface) of the balloon. The balloon covered imaging system can be applied to various types of minimal invasive surgical interventions and diagnosis procedures, particularly where materials (e.g., blood, calcium deposition, and tissue flaps) need to be removed, and/or the procedure needs to be monitored in order to achieve optimum outcome. Examples of such procedures include angioplastic procedure, vascular stenting procedure, and balloon heart valve replacement procedure.

One embodiment includes an imaging system having a projector configured to project an illumination pattern or markings (e.g., a gridline) onto a surface within a field of view of one or more lenses of the imaging system. Various techniques are well known for projecting illumination patterns from very small objects, ranging from simple techniques such as one or more LEDs or lasers projected through one or more fixed image pattern die (possibly including diffusers and/or mirror assemblies), to more sophisticated configurable techniques such as using liquid crystal on silicon (LCOS) or DLP technologies. The technique of using illumination pattern projection can be applied to various types of minimal invasive procedures, particularly procedures that require one or more of subject surface image characterization, 2-D rendering, 3D rendering or dimensionally proportionate or dimensionally accurate imaging at procedure site. In some embodiments, this technique is applied in procedures for body spaces where the fluid is translucent, such as joint fluid or air. Examples of such procedures include arthroscopic shoulder surgery and knee surgery where the fluid at the surgical sites is clear and allows for good visibility of the surrounding tissues, or abdominal surgery where there can be air spaces (or gas spaces) in which to perform the procedure.

One embodiment includes an imaging system that is capable of capturing overlapping images from multiple lens locations, either by sequentially taking images as the lens is moving from one location to another or by using multiple lenses with overlapping fields of view to capture multiple images simultaneously. This spatial sampling of images from different perspectives can improve image resolution and can be used to generate various forms of 3D imaging such as surface images, cross sections and 3D solid models. This embodiment may also be used to enhance the resolution or accuracy of conventional visual images. In addition imaging embodiments that have multiple lenses with overlapping fields of view are particularly suited for rapid real-time imaging with wide viewing angle, such as during balloon heart valve replacement surgery where rapid and accurate characterization of the surgical site before and during the surgery is important for ensuring patient safety.

In some embodiments, the imaging system includes an image processing unit configured to correct for image distortion as a function of optical lens view angle that result from close proximity of subject and lens. This embodiment is also beneficial for situations where wide angle lenses are used and/or images are captured close to the lens, such as during various minimal invasive procedures.

The embodiments discussed herein can be combined in various ways to achieve optimum imaging results. In one example, an imaging system that combines the balloon covered camera system, gridline assisted imaging, multiple lenses with overlapping fields of view, and image distortion correction can be used for heart valve replacement surgery and vascular stenting procedure where accurate real-time characterization of the surgical site before, during and after the surgery is advantageous.

In some embodiments, an optical composite method can be used to generate an image. A digitally constructed improved composite image can be obtained by digitally superimposing at least two optical images. In some embodiments, each image is obtained from a CCD camera matrix that captures the image from a lens apparatus on the device. In some embodiments, the composite image may be further improved by a process where each individual optical image or the composite image is digitally corrected with an error reduction algorithm to account for imperfections in the image, with an input for the error reduction algorithm being obtained from a calibration procedure performed on the device.

In some embodiments, an optical imaging calibration procedure is used. Such a procedure can include positioning a device near or within a physical calibration subject (also referred to herein as a "calibration target assembly") of known surface dimensions, with the imaging device located in a known relative position with respect to the calibration subject, and measuring a difference between the known physical properties of the calibration subject and digitized versions of the images taken from the device. In further embodiments, one or more algorithms are applied to determine a calibration correction factor to be applied to the individual images or a composite image, and thus minimize the error between the known calibration subject features and the digitally constructed composite image. In some embodiments, one goal of the calibration procedure may be to provide a more accurate relative image, and/or to provide an absolute dimensional reference for the image.

In some embodiments, a composite digital image error reduction procedure is used. In such a procedure, at least two digital images are received from two or more optical sensors on the device. A common feature present in an overlapping view region may be identified from the at least two images. The size and shape of the common feature can be determined by observing the view angle and pixel features and/or extent from the at least two images, and then applying a correction factor to other elements of the composite image and/or applying a correction factor to other digitized images received from individual image sensors.

In some embodiments, the calibration subject may be a cavity of known interior dimensions, and in the case where the imaging device is in a form intended for imaging internal body cavities this can be advantageous. In yet further embodiments, the calibration subject is may be another 3-dimensional figure that is viewed by at least two lenses in the imaging device. In yet further embodiments, the calibration subject may have a physical feature that is non-uniform (also referred to herein as a "nodule" and "cavity") in order to provide a non-unifoiin feature reference in the image sensor data used for calibration. In yet further embodiments, multiple calibration subjects may be imaged by the device in a manner similar to that described above in order to collect additional information on the error between known physical properties of the calibration subject and a digitized version of the images taken from the device for multiple calibration conditions. For example, multiple calibration subjects with multiple features can provide more than one set of data to fit to a multi-variable error curve. As another example, multiple calibration subjects with multiple features can provide more than one set of data to fit to a multi-variable absolute position and dimension algorithm used to define the absolute position and dimensions of features that are in the common view field of at least two image sensors.

In some embodiments, ultrasound imaging can be advantageously used, for example, in circumstances where the physical medium in the body cavity is not completely clear or is opaque, such as cavities, arteries or vessels filled with blood or non-clear body fluids. Ultrasound imaging also has the advantage of providing absolute distances for return signals to aid in determining the absolute physical properties of an image subject. In some embodiments, a digitally constructed composite image is generated by digitally superimposing two or more (at least two) sets of ultrasound transducer signals, each set of transducer return signals obtained from a digitization of a sequence of beam scans from an ultrasound transducer array. Each transducer array consist of multiple phased array elements of a similar individual ultrasound transducer composition, with the transducer array having the ability to steer a beam by modulating the phase, and possibly amplitude, of the individual sonic signals transmitted and/or received from each individual array element. Further. each beam scan may cover a different angular beam-region of an imaging subject.

In some embodiments, the two or more sets of ultrasound transducer signals are digitally image processed to identify common features in the overlapping view region of the at least two ultrasound transducer arrays and the signals from the common features are digitally superimposed and further processed to create an enhanced composite image. In yet further embodiments, each of the two or more sets of digitized scanned ultrasound transducer array signals are digitally image processed to form an individual digital image, and the two or more digital images are then superimposed to form an improved composite image. In some embodiments, the composite image formed from the multiple ultrasound transducers may be further improved by digitally correcting each individual image constructed from the ultrasound transducer signals (or the composite image formed from the two individual ultrasound transducer signals) with an error reduction algorithm to account for imperfections in the image. This may be performed by using an input for the error reduction algorithm that is obtained from a calibration procedure performed on the device.

In some embodiments, a calibration procedure can be used that is applicable to various types of signals, including both optical and ultrasound signals. In some embodiments, such a procedure includes positioning the device near or within a physical calibration subject of known surface dimensions. The imaging device may be positioned in a known relative position with respect to the calibration subject, and a difference is measured between the known physical properties of the calibration subject and a digitized versions of the images taken from the device. In yet further embodiments, various algorithms are applied to determine a calibration correction factor to be applied to the individual images or a composite image to minimize the error between the know calibration subject features and the digitally constructed composite image. In some embodiments, one goal of a calibration procedure may be to provide a more accurate relative image, or to provide an absolute dimensional reference for the image.

In some embodiments, ultrasound composite imaging can be used to generate images having reduced errors. One composite digital image error reduction procedure includes receiving at least two ultrasound transducer signals on the device and processing these signals to form respective digital images. A common feature present in an overlapping view region of the images can be identified by determining the size and shape of the common feature based on observation of the view angle and pixel features and/or extent from the at least two images, and then applying a correction factor to other elements of the composite image and/or applying a correction factor to other digitized images formed from the individual ultrasound transducer signals.

In some embodiments, ultrasound composite imaging can be further employed. A calibration subject may be a cavity of known interior dimensions, where in the case where the imaging device is in a form intended for imaging internal body cavities, for example, this can be advantageous. In some embodiments, the calibration subject is may be another 3-dimensional figure that is viewed by at least two lenses in the imaging device. In yet further embodiments, the calibration subject may have a physical feature that is non-uniform (also referred to elsewhere herein as a "nodule") in order to provide a non-uniform feature reference in the image sensor data used for calibration. In yet further embodiments, multiple calibration subjects may be imaged by the device in a manner similar to that described above in order to collect additional information on the error between known physical properties of the calibration subject and a digitized version of the images taken from the device for multiple calibration conditions. For example, multiple calibration subjects with multiple features can provide more than one set of data to fit to a multi-variable error curve. As another example, multiple calibration subjects with multiple features can provide more than one set of data to fit to a multi-variable absolute position and dimension algorithm used to define the absolute position and dimensions of features that are in the common view field of at least two image sensors.

In some embodiments, aspects of calibration procedures may be applicable to various types of signals, including both optical and ultrasound signals. The device calibration procedures described herein may be applied once to a given device design to determine a set of error correction data, error correction curve fit or error correction algorithm parameters that are to be applied to the device design for all devices manufactured. The device calibration procedures described herein may be applied to each individual device after it is manufactured to determine the error correction data, curve or algorithm parameters to be applied to an individual device, and in this case errors due to manufacturing tolerances can be calibrated out to a larger degree.

In some embodiments, image display aspects are common to various types of signals, including both optical and ultrasound signals. In some embodiments using ultrasound composite imaging, the digitally constructed image is rendered in various display formats with the use of digital image processing algorithms. These aspects of the method may include displaying a rendering of a 3-D composite image, with a view angle and magnification that is selectable by an imaging display user. These aspects of the method may also include creating a contour image rendering, a cross sectional image rendering and/or another image rendering, any of which may also be rotated and magnified by the imaging display user. In any of these aspects of the invention, an absolute dimensional reference may be displayed with the image, or the image may include an absolute dimensional reference coordinate system.

It should be understood, that other imaging transducers, illuminators or sensors can be used in place of the optical and ultrasound embodiments described herein. For example, LIDAR techniques can be applied in a multiple-sensor device configuration in much the same manner, and the calibration techniques, image processing techniques, and other techniques described herein could also be applied to LIDAR.

Figure 1B:
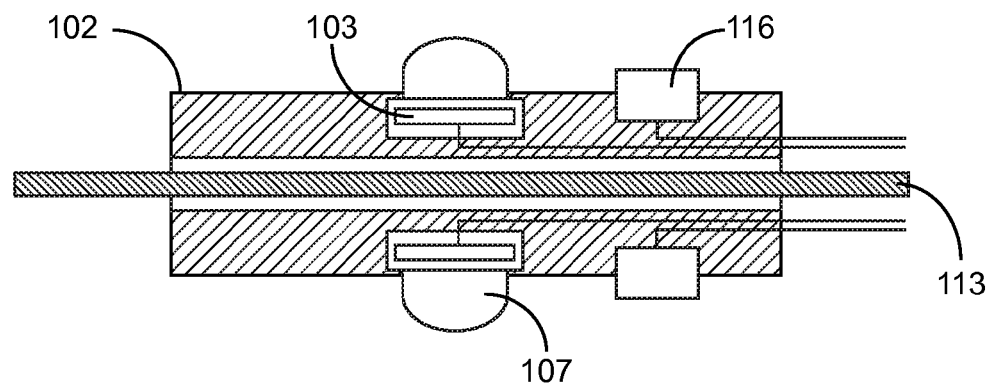
Figure 1C:
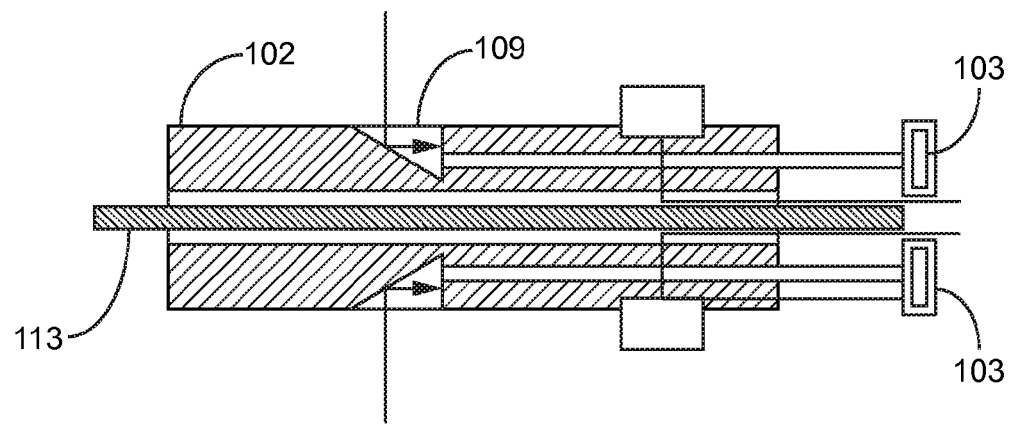

FIGS. 1A-1C illustrate aspects of an embodiment of an imaging system 100. The imaging system 100 as shown includes an array manifold 102. As show in in FIGS. 1B and 1C, the array manifold 100 can hold an array of lenses 104 coupled to one or more imaging sensors 103. The imaging sensors 103 may be optical imaging sensors, such as one or more CCD or APS (CMOS) imaging sensors, directly coupled to the one or lenses 104 or indirectly coupled via a light transmitting medium such as fiber optic fibers, glass rods or other optical transmission media or optical cables. The imaging sensors 103 can be configured to receive white light or infrared light. Prism lenses may be used in some embodiments to direct the image from the lens to an optical transmission media or directly to the optical imaging sensors. The imaging sensors 103 can be composed of a variety of mechanisms, including for example CCD integrated circuits or miniature CCD integrated circuits often employed in arthroscopic and laparoscopic imaging. The one or more lenses 104 can include of various suitable lenses, such as wide-angle lenses (107 FIG. 1B), fiber optical lens, prism lens (109 of FIG. 1C), and glass rod lens.

It should be understood that other non-optical imaging sensors 103 could also be used in various embodiments. Such non-optical imaging sensors can include piezoelectric devices configured to receive and/or emit various types of energy, such as sonar or ultrasonic energy. Further, each imaging sensor 103 may be a sub-array of a plurality of sensors.

In some embodiments, the array manifold 102 can be covered with a balloon 106 made of an expandable elastic material and mounted on the body of an elongated catheter 108 (full length not shown) for aiding the insertion of the imaging system into a body cavity such as an intravascular space (e.g., intravenous, intra-arterial, intra-atrial, and intra-ventricular space). The balloon 106 may possesses elastic properties that allow the expandable covering to expand and contract. The balloon 106 is in fluid communication with a pressurizable fluid chamber 110 via a fluid channel 111. The balloon 106 expands when the fluid inside the fluid chamber 110 is pressurized and the fluid is pumped into the balloon. The fluid can be a gas such as air, an alternate gas, or a liquid such as a sterile saline solution. In some embodiments, the balloon 106 includes markings 114 that contrast from the inner balloon surface and having a pattern that changes, e.g., expands and contracts as the balloon 106 expands and contracts. In some embodiments, markings 114 are visible on the interior surface of the balloon 106 (e.g., printed on a interior surface of the balloon 106 or created from balloon skin materials of differing colors formed into a pattern) so that the pattern is visible within at least a portion of the field of view of one or more lenses 104 of the imaging system 100.

In some embodiments, the balloon 106 can be constructed from a semi-compliant or non-compliant material, and is not limited to compliant materials. In some embodiments, the balloon 106 is inflated until it provides sufficient contact with the subject being imaged (e.g., the interior of an artery, the interior of a ventricle, a heart valve, etc.) such that the balloon conforms to the subject being imaged so that it takes on the shape of the subject. This allows evacuation of non-translucent fluids (e.g., blood) so that the subject may be optically imaged. Such embodiments are useful for examples such as imaging the interior of an artery, imaging the interior of a body space that contains a non-translucent or semi-translucent fluid, imaging the interior of a ventricle, imaging a heart valve, etc. However, It should be understood, that the balloon 106 is not required for imaging, particularly when non-optical imaging sensors are used.

In some embodiments, the images obtained may be enhanced by using the balloon 106 with reference markings 114, such as marked patterns, or projecting an illumination pattern from the apparatus within the balloon. Such reference markings 114 or illumination patterns may be used to help resolve the surface properties of the subject being imaged, or may be used to aid in determining the physical dimensions of the subject being imaged. The markings or illumination patterns that exist in images captured with such embodiments may be used to aid the digital signal processing of the images because the reference markings 114 or illumination patterns provide advantageous image properties such as improved contrast of surface properties, physical reference dimensions, ability to ascertain distance from lens to subject, etc.

In some embodiments, the balloon 106 is an angioplastic balloon for removing vascular blockage and the imaging system can be used to characterize the angioplastic site and monitor the progress or effectiveness of the angioplastic procedure. In such embodiments, the balloon 106 construction may be optimized to provide sufficient pliability so that it conforms to the surface of the imaging subject and also to provide sufficient force to expand the artery or vessel inclusive of the material that is being removed (for example plaque, calcium deposits and other such material).

In some embodiments, the expandable covering includes a balloon used for deploying a stent to re-enforce weak vascular wall and the imaging system can be used to characterize the stent site and monitor the progress of the stenting procedure. In such embodiments, the balloon construction may be optimized to provide sufficient pliability so that it conforms to the surface of the imaging subject and also to provide sufficient force to expand and install the stent. In some embodiments, the imaging system may be used to monitor the stent installation procedure or the effectiveness of the stent installation.

In some embodiments, the expandable covering includes a balloon used for deploying heart valve and the imaging system can be used for characterizing the tissue at the prosthetic heart valve replacement site for selecting the appropriate replacement heart valve and heart valve deployment parameters. In such embodiments, the balloon construction may be optimized to provide sufficient pliability so that it conforms to the surface of the imaging subject and also to provide sufficient force to expand and install the prosthetic heart valve. In some embodiments, the imaging system may be used to monitor the prosthetic heart valve installation procedure or the effectiveness of the prosthetic heart valve or the position of the installed prosthetic heart valve.

In some embodiments, the imaging system 100 can also include an imaging transmission device 116 configured to provide imaging energy for the imaging sensors 104 to process. In some embodiments, an imaging transmission device 116 is used to illuminate the field of view of the one or more lenses 104 of the imaging system 100 by providing white or infrared light. In other embodiments, an imaging transmission device 116 provides sonar waves or ultrasonic energy via a vibrating surface, such as a speaker or piezoelectric element.

At least one energy transmission device 116 can be used, while in other embodiments a plurality is used (e.g., at least one per imaging sensor). In some embodiments, at least a subset of the one or more imaging transmission devices 116 are configured to project a marking (e.g., gridline) onto an adjacent surface such as an interior surface of the balloon placed over the lens or onto a surface of the characterization site.

In some embodiments, reference markings 114, either drawn on the balloon 106, projected onto a surface of the balloon 106 or projected onto a surface of the characterization site, can be used to aid the interpretation of the camera images and resolving underlying features on the characterization surface. The reference markings 114 drawn on the balloon 106 can include any suitable patterns having features with defined spatial separation that will provide a useful mapping of the image proportion and the actual dimension. The reference markings 114 can include various sizes of dots, circles, triangles, angularly separated features, meshes and various other patterns. The projected marking can also include any suitable patterns having features with defined spatial separation as a function of distance from the projection origin that will provide a useful mapping of image proportion and the actual dimension. For example, it can include various sizes of dots, circles, triangles, meshes and various other patterns.

The imaging system 100 may further include a processor 118 coupled to a memory 120 and a display 122. The processor 118 may include a controller for controlling the operation of the imaging system 100 such as a lens controller for controlling the operation of the one or more lens 104, an imaging transmission controller for controlling the operation of the one or more imaging transmission devices 116, and a balloon inflation controller for providing closed pressure control to cause the balloon 106 to inflate or deflate as needed. The processor 118 may further include an image processor for recording the images captured by the one or more lenses 104 and for processing the images, including for example removing image distortions, mapping gridline contour to underlying image features, resolving true dimensionality of images, synthesizing a composite image from multiple overlapping images, and rendering the images for display. Methods described herein can be codified into machine instructions that can be physically stored in the memory 120. In turn, the processor 118 is configured to execute these instructions to perform the related methods.

In some embodiments, the catheter 108 may also include various tools such as a guide wire 113 for guiding the catheter, a second balloon (not shown), a laser (not shown), and a drug delivery port (not shown). The various tools can be incorporated into the catheter 108 depending on the surgical or diagnosis need of a particular situation. In this way the imaging system 100 can be multifunctional.

Figure 2:
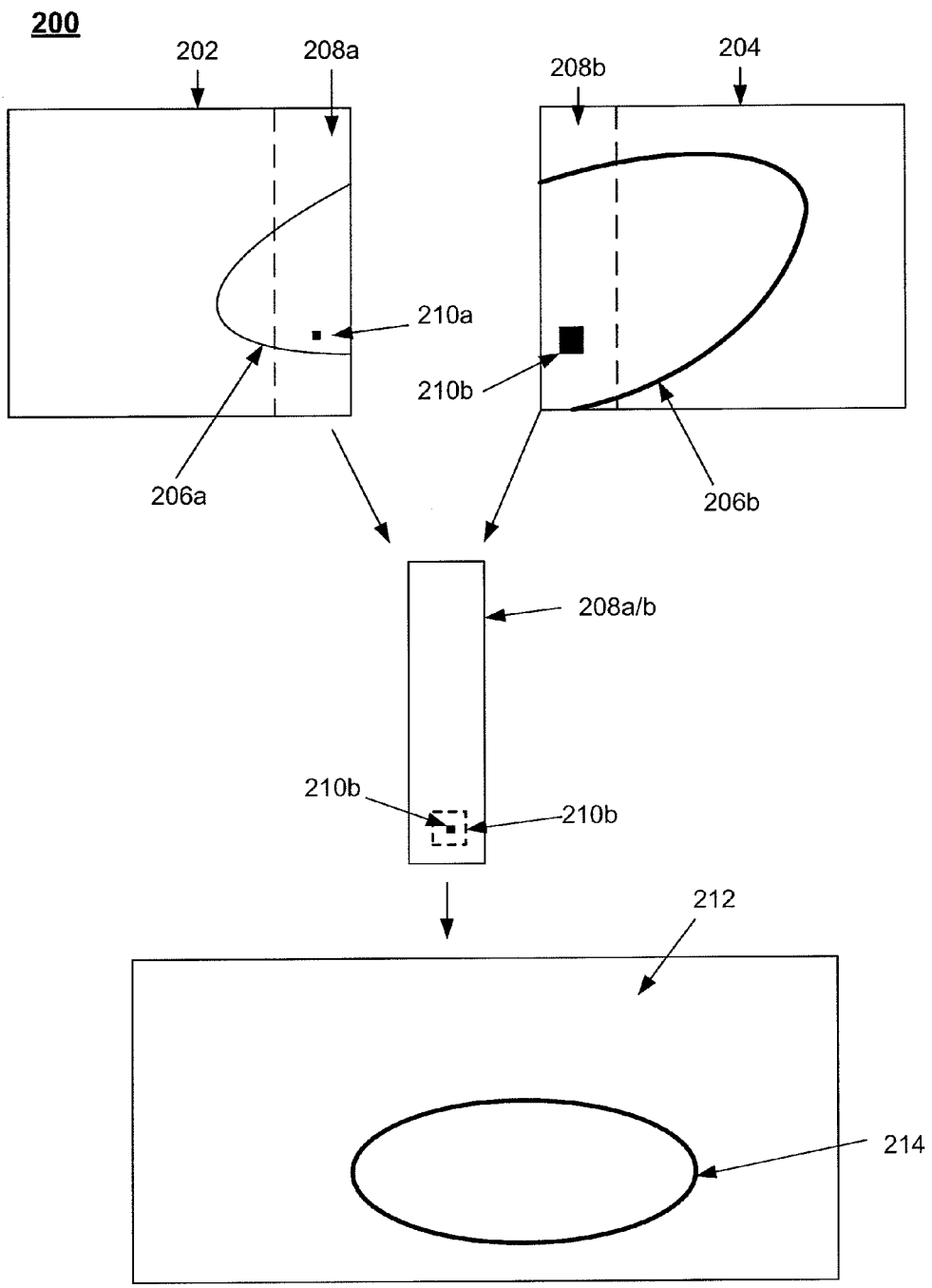
FIG. 2 is a simplified schematic representation of a method for creating an image.

Image Generation Methods:

FIG. 2 illustrates an embodiment of a method 200 for generating an image. By way of example, the imaging sensors 103 of the imaging system 100 may be used to generate a plurality of images, which for the sake of simplicity is shown here as a first image 202 and a second image 204. However, it should be understood that the method is applicable to a greater amount of images. Since each imaging sensor 103 can have a distinct and partially overlapping field of view, the first image 202 and the second image 204 both include aspects 206a/206b of a contiguous imaged aspect. Each image also includes a partially overlapping zone 208a/208b. The non-overlapping portions of each image represent imaged portions that are out of operation range of an adjacent imaging sensor.

Typically, the images 206a/206b are digitally captured and thus pixilated. Pixels and pixel clusters can be used to calibrate such images. Here, a pixel 210a of zone 208a is identified to be an image of the same image sub-aspect as pixel cluster 210b of zone 208b. The image sub-aspect, may for example be of reference markings of a balloon. Similar aspects in the overlapping zones 208a/208b can be identified and used to calibrate the first and second images into a greater image. But it should be understood that additional aspects can also be identified, and that what is shown is a simplified example.

As shown, there are size and positional differences between the imaged aspects of pixel 210a and 210b. This may be, for example, because of differences in distance from respective imaging sensors to the imaged aspect. Accordingly, further interpolation is applied to adjust dimensionality and position of each image, or one image, such that the first image 202 and the second image 206 can be used to produce a final calibrated image 212 that shows the contiguous imaged aspect 214 in a calibrated form. It should be understood that method 200 can be applied in a real-time basis to calibrate a steam of images (i.e., video image), such that an operator of an associated device may operate the device in a patient using the guidance of the calibrated live action video stream.

Figure 3A:
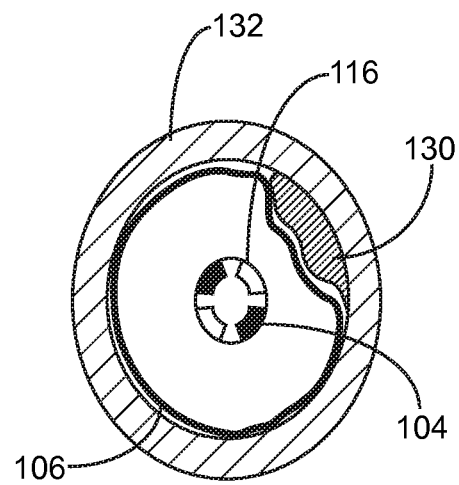
FIG. 3A is a cross section of a body cavity imaged using an imaging system in accordance with some embodiments.
Figure 3B:
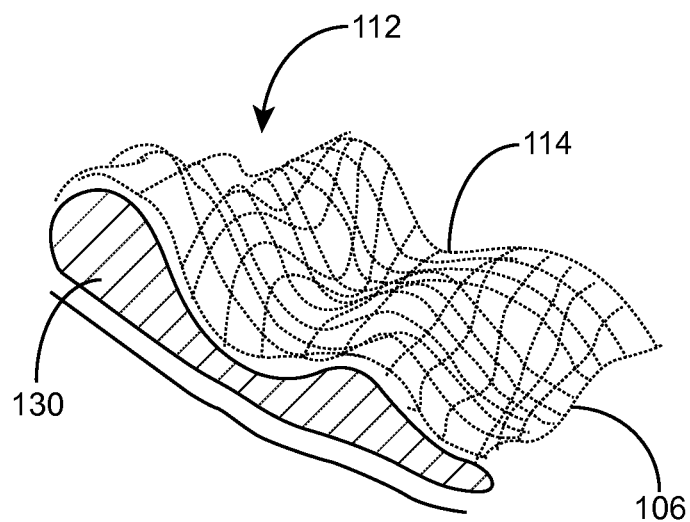
FIG. 3B illustrates a section of a balloon as it conforms to the shape of an underlying feature in accordance with some embodiments.

Imaging inside the small space of a body cavity can pose various challenges. For example, the lighting may not be good inside the cavity and the shadow can be created, making it difficult to resolve features on the surface of the cavity. The pattern formed by the markings can be used to resolve the underlying features. As the balloon expands inside a body cavity 132, it touches and conforms to interior surface of the cavity, illustrated in FIG. 3A. As the balloon takes on the shape of the underlying features on the surface of the cavity, the pattern formed by the markings (e.g., gridlines) will deform differently depending on the underlying features of the cavity interior surface. This distortion in the marking pattern can help to resolve features on the surface of the body cavity. FIG. 3B illustrates a section of the balloon conformation to the shape of the underlying features 130 and that the grid line 114 distortion varies as the shape of the underlying feature 130 changes. The gridline distortion can be used to resolve the underlying features.

As the balloon expands inside a body cavity, the spacing between the markings increase and can be used as a reference or calibration for determining the absolute dimension of a feature imaged by the imaging system 100. The absolute distance between two markings can be calibrated using various digital image processing techniques. Such techniques will be readily known to one or ordinary skill in the art. For example purposes not intended to be limiting in any way, a simple image processing algorithm class may be employed in some embodiments that is based on various methods of essentially determining the pixel separation of various pattern configurations present in the balloon markings that are captured on the camera image. The more pixel separation, the further away the markings are from the lens and the larger the distance between the markings. The absolute dimension of an imaged feature can then be determined based the calibrated distance between the markings.

In one example, the pixel separation generated in the image captured by two adjacent dots on the markings can be used to calibrate the absolute distance between the two dots, which in turn can be used to measure or calibrate the absolute dimension of the features imaged. In some embodiments, image processing algorithms are employed that use more sophisticated techniques such as various algorithms that can determine not only the distance to the image and physical separation between marking pattern elements, but also determine the surface shape of the image subject based on capturing the shapes of the marking patterns as deformed by contact and conformance with the image subject surface, and ascertaining the underlying surface shape that causes the deformation observed in the shapes of the marking patterns. Such embodiments may also include determination of not only the relative shape of the subject surface, but also the absolute physical dimensions of the features in the subject surface. Once the subject surface image is thus ascertained, additional image processing algorithms may be employed in some embodiments to create various renderings of the subject, such as surface renderings, 3D solids model renderings, various cross section renderings, etc.

When embodiments that employ illumination pattern projection as described herein are deployed, image processing techniques and algorithms similar to those described above for balloon embodiments with marking may be employed to map observed illumination pattern shapes captured in the camera images, where the illumination patterns are deformed by projection onto the image subject surface.

Calibration:

In some embodiments, the systems and devices disclosed herein are calibrated prior to use. Calibration may be required since each imaging sensor may not have ideal alignment on an array manifold, and further the balloon may not have ideally arranged reference markings. In some embodiments, the calibration is carried out in-situ the help of a calibration target assembly that the lens system is inserted into, where the calibration target assembly may have marking patterns or illumination patterns or various physical configurations of the target surface.

In some embodiments, the calibration target assembly is a simplified cavity having a plurality of target subjects. By imaging such target subjects with known physical parameters, correction algorithms may be applied to correct any deviations between the known properties of the target and the physical or image properties ascertained by the imaging system, where the deviations may be caused by one or more of lens distortion, lens placement, manufacturing tolerances, imaging system imperfections, etc. In some embodiments, at least one calibration target is placed within a field of view of at least one of the one or more lenses of imaging system. In some embodiments, calibration targets are placed at multiple locations within a view of at least one or more lenses of the imaging system. In some embodiments, calibration is carried out outside of an operating environment of the imaging system. In some embodiments, calibration is based on a predetermined distortion pattern of one or more lenses.

Figure 3C:
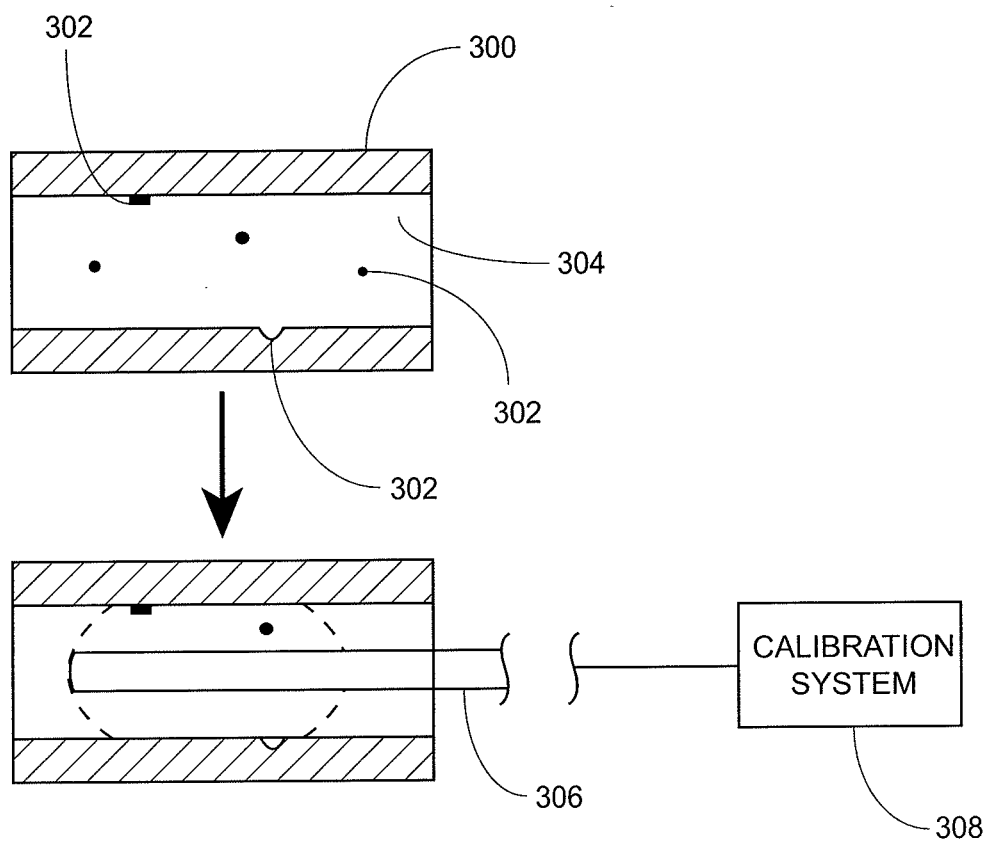
FIGS. 3C and 3D are schematic diagrams of methods to calibrate a device, in accordance with some embodiments.
Figure 3D:
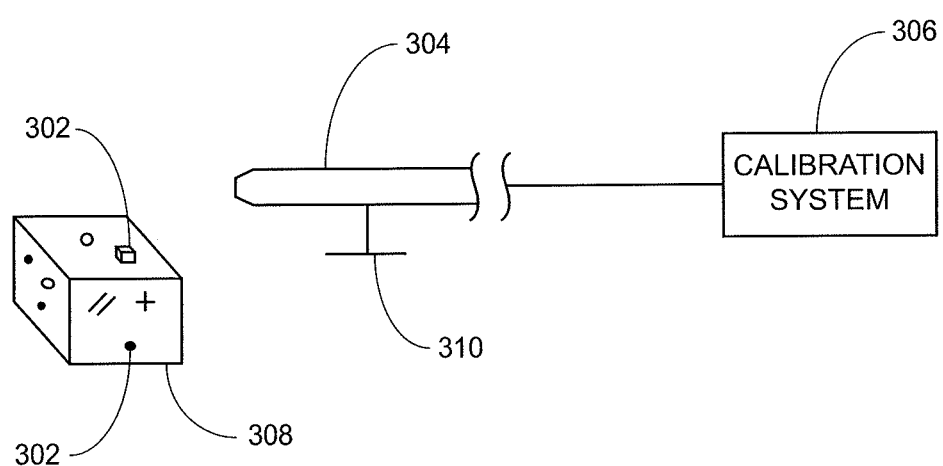

FIG. 3C show a method of calibration, according an embodiments of the invention. In exemplary use, a device having a plurality of angularly and axially separated imaging sensors is inserted into a calibration target assembly 300. Such an assembly 300 can take the form of a cylinder 300, shown herein in cross-section, having 2D and/or 3D calibration reference markings 302 located on a surface 304, such as the inner surface of the cylinder 300. In some embodiments, reference markings 302 may take the form of markings, nodules, cavities, and roughed surfaces. The calibration target assembly 300 may be filled or immersed with a transmission fluid to simulate a working environment, such as saline or carbon dioxide gas. The device 306 can be used to generate a plurality of images for which a calibration factor can be generated from by a coupled calibration system 308.

FIG. 3C show another method of calibration, according an embodiments of the invention. In this embodiment, the calibration target assembly 308 is configured to be externally adjacent to the device 3D. Such an assembly 308 can take many forms, and is shown here as a block for the sake of simplicity. The calibration target assembly 308 and device 304 may be within a greater housing that is filled or immersed with a transmission fluid to simulate a working environment, such as saline or carbon dioxide gas. In some embodiments the device 304 is held into a stable position by a frame or jig 310 of known dimensionality with respect to the calibration target assembly 308. Several jigs 310 may be used to manually or robotically place the device 304 into various different known positions about the calibration target assembly 308. Additionally or alternatively, the calibration target assembly 308 can be manually or robotically placed into various different positions about the device 304. In such embodiments, the calibration system can be configured to robotically position the device 304 and/or calibration target assembly.

Generally, the calibration target assembly should be configured such that each imaging sensor is placed with a respective field of view of at least one calibration reference or plurality of calibration reference. The device is then operated to generate images of the calibration references. After the images are generated, the imaged calibration reference can be analyzed to determine imaging sensor accuracy from which an imaging correction factor is derived from. Such an imaging correction factor may include a plurality of sub-correctional factors for various dimensional aspects for various imaging sensors. The imaging correction factor can be applied to later generated images generated by the device. In this way, the correction factor can be used to resolve issues of manufacturing variances, such as spacing and angular alignment, between the imaging sensors and a surrounding structure and/or substructures, as well as other physical characteristics.

In some embodiments, the device to be calibrated includes a balloon with reference markings covering the fields of view of the plurality of imaging sensors. Thus, in embodiments where 3D calibration references are present on a calibration surface of the calibration target assembly, a generated image includes images of distortions of the 3D calibration references. The imaged distortions can be then compared with values corresponding to ideal values, and from this a correction factor can be generated. Further, in some embodiments, the 3D calibration references may be constructed from pliable materials as compared to the calibration surface of the calibration target assembly. Expansion of the balloon causes deformation of these pliable calibration references, which are imaged by the device for calibration and generation of a correction factor. Such a correction factor can then take into account variable physical characteristics of the balloon that may cause variations for imaging. By this way, for example, manufacturing variances of balloon wall thickness and/or balloon shape can be accounted for.

It should be understood that the calibration methods disclosed herein can be performed with completed devices, such as catheters, as well as sub-assemblies, such as a imaging sensor manifold. Further, these methods can be applied in the field of use or in a manufacturing setting. The correction factor can be codified as instructions into physical memory (e.g., microchip) of a device, or stored on a network, that communicatively interfaces (physically or remotely) with an imaging system, which is configured to account for the correction factor when generating an image. Upon such an interface, the imaging system may access the information stored on the physical memory, or downloaded into imaging system memory, for performing the calibration. In other embodiments, calibration can be performed in the field of use (e.g., operating room). In such instances, the imaging system is configured to perform calibration for generation of a correction factor.

Alternative Embodiments

FIGS. 4A through 4E illustrate imaging systems in accordance with some embodiments. These systems are generally constructed as recited with respect to the imaging system 100 shown in FIGS. 1A-1C, however with differentiations as described below.

Figure 4A:
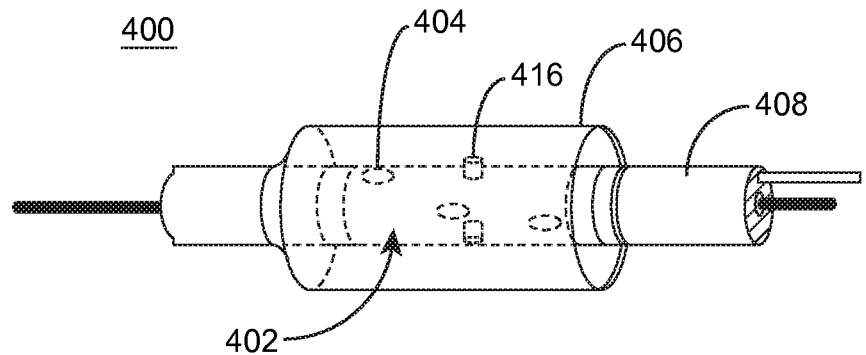
FIGS. 4A-4I illustrate imaging systems according to various embodiments.

FIG. 4A illustrates an alternative embodiment of an imaging system 400 having an array manifold 402 holding a plurality of imaging sensors 404 covered by a balloon 406. The array of imaging sensors 404 are angularly (by 120 degree) and axially spaced on the array manifold 402, and imaging transmission devices 408 that are angularly spaced (by 180 degree). Reference markings (not shown) are projectable onto the interior surface of the balloon 406 by the imaging transmission devices 416.

Figure 4B:
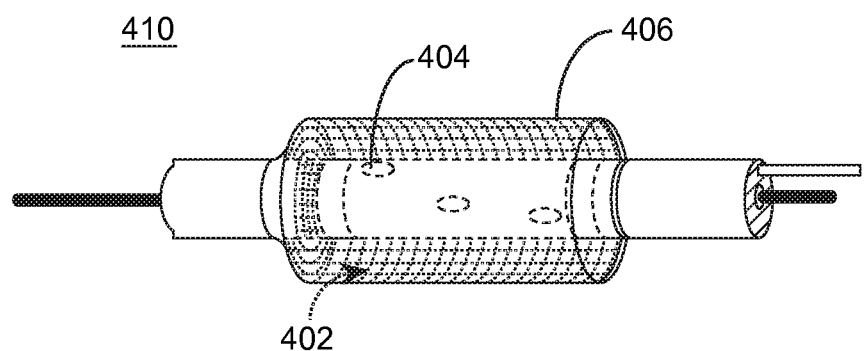

FIG. 4B illustrates an embodiment of the imaging system 412 with three angularly spaced (by 120 degree) lenses 404, in a similar configuration to the imaging system 400, however, this embodiment does not include separate imaging transmission devices, which are incorporated into the lens 404, or alternatively purposely left out in the case, for example, where another light source is provided, such as from an adjacent scope in a laparoscopic procedure. Further, in this embodiment markings 414 are drawn onto the interior surface of the balloon 406.

Figure 4C:
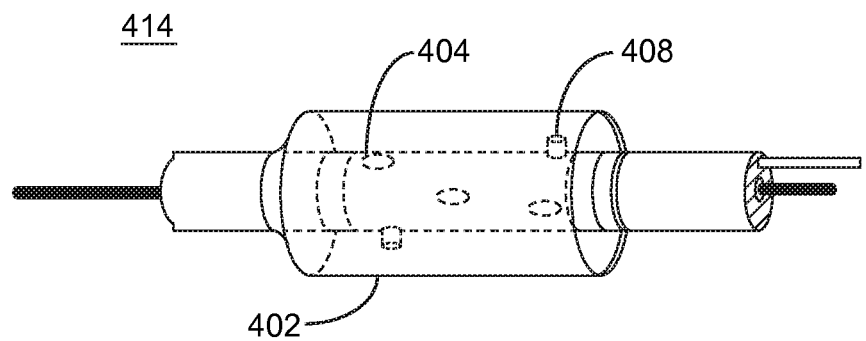

FIG. 4C illustrates an embodiment of the imaging system 414 having 3 angularly spaced and axially spaced lenses 404 and two angularly spaced and axially spaced imaging transmission devices 408. Reference markings (not shown) are projectable onto the surface of the characterization site directly using the imaging transmission devices 408.

Figure 4D:
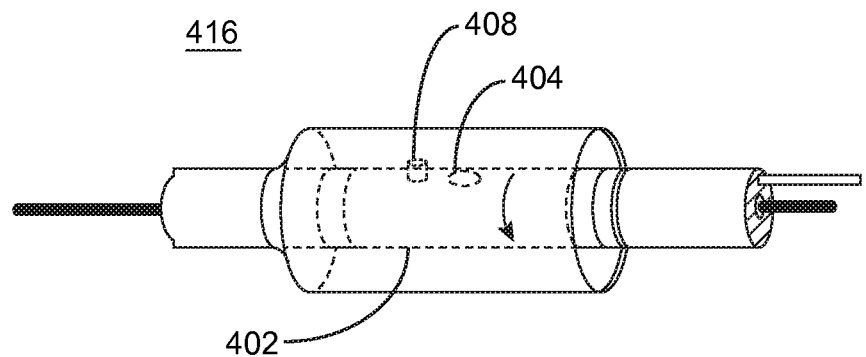

FIG. 4D illustrates an embodiment of the imaging system 416 having one lens 404 and one imaging transmission device 408. Reference markings (now shown) are projectable onto the interior surface of the expandable covering. In this example, the array manifold 402 can rotate along the axial axis relative to the catheter while images are being captured (the rotation mechanism not shown). The array manifold 402 can be rotated, for example, by a wire connected thereto, which is driven by a motor. This arrangement allows for multiple-location image sampling for achieving improved image resolution. The captured image can be used to render a 3D surface contour of the balloon surface after it assumes the shape of the surface of the characterization site.

Figure 4E:
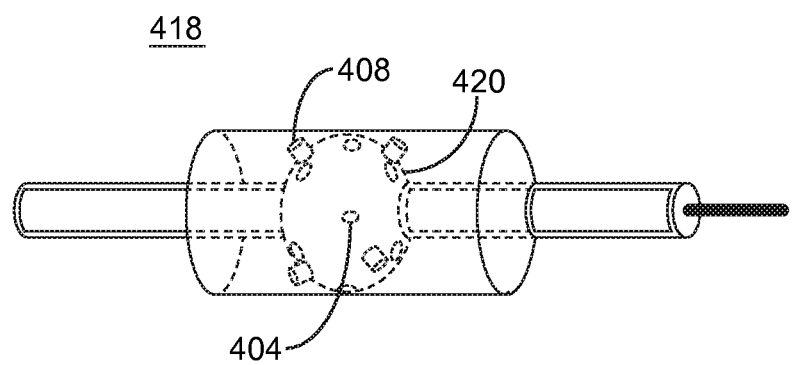

FIG. 4E illustrates an embodiment of the imaging system 418 having a system 418 with spherical array manifold 420. The spherical array manifold 420 provides the lens array 404 with a unique field of vision.

Figure 4F:
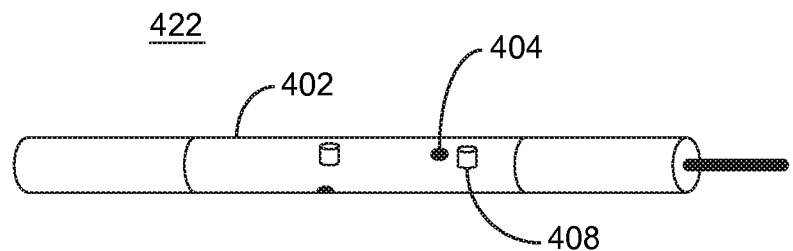

FIG. 4F illustrates an embodiment of an imaging system 422 which has no balloon. In absence of the balloon, the imaging system 422 can be configured similarly to any of the configurations disclosed herein.

Figure 4G:
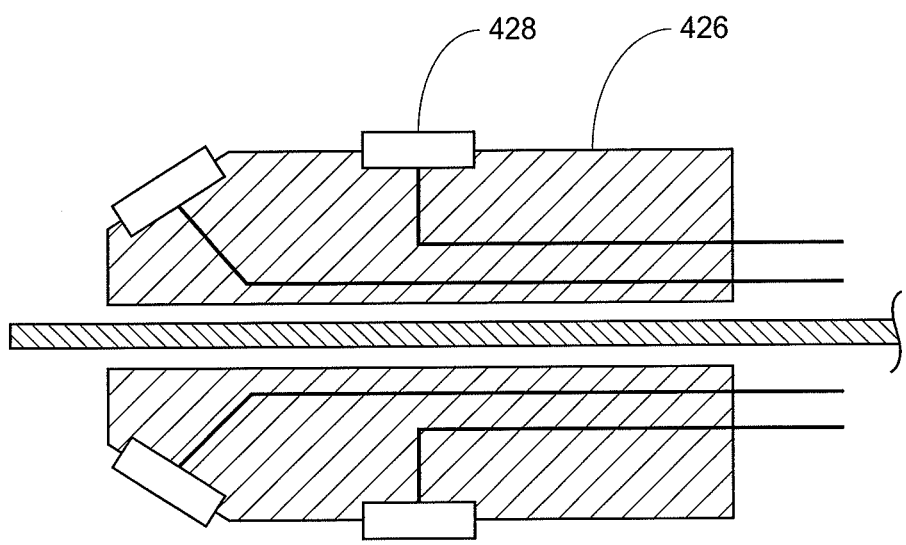

FIG. 4G illustrates an embodiment of an imaging system 424 that includes an array manifold 426 configured to hold plurality of imaging sensors 428 in the form of ultrasound transducers. The ultrasound transducers are configured to have overlapping fields of view. A portion of the array manifold 426 is beveled to provide some transducers with a forward facing field of view. The bevel angle can be various angles of degrees, for example, 45°. However, other bevels and shapes are possible, such as double beveled manifolds.

Figure 4H:
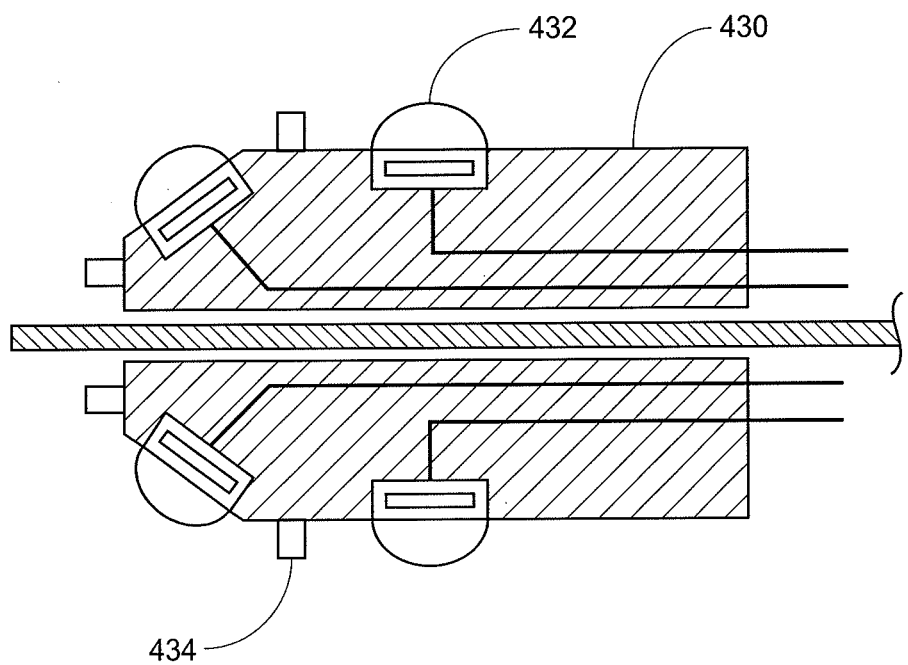

In a similar manner, the imaging system 428 of FIG. 4H includes an array manifold 430 that is configured to hold a plurality of imaging sensors 432 in the form of optical imaging sensors. The optical imaging sensors are configured to have overlapping fields of view. A portion of the array manifold 430 is beveled to provide some optical imaging sensors with a forward facing field of view. Illuminators 434 can be positioned in a similar manner to the optical imaging sensors, to provide the imaging sensors with a light source. The bevel angle can be various angles of degrees, for example, 45°. However, other bevels and shapes are possible, such as double beveled manifolds.

Figure 4I:
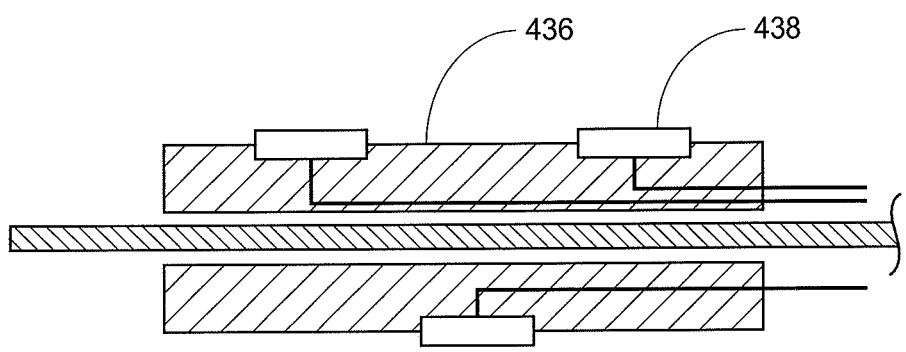

FIG. 4I illustrates an embodiment of an imaging system 434 that includes an array manifold 436 configured to hold plurality of imaging sensors 438 with radially positioned ultrasonic transducers. The ultrasound transducers are configured to have overlapping fields of view.

Figure 4J:
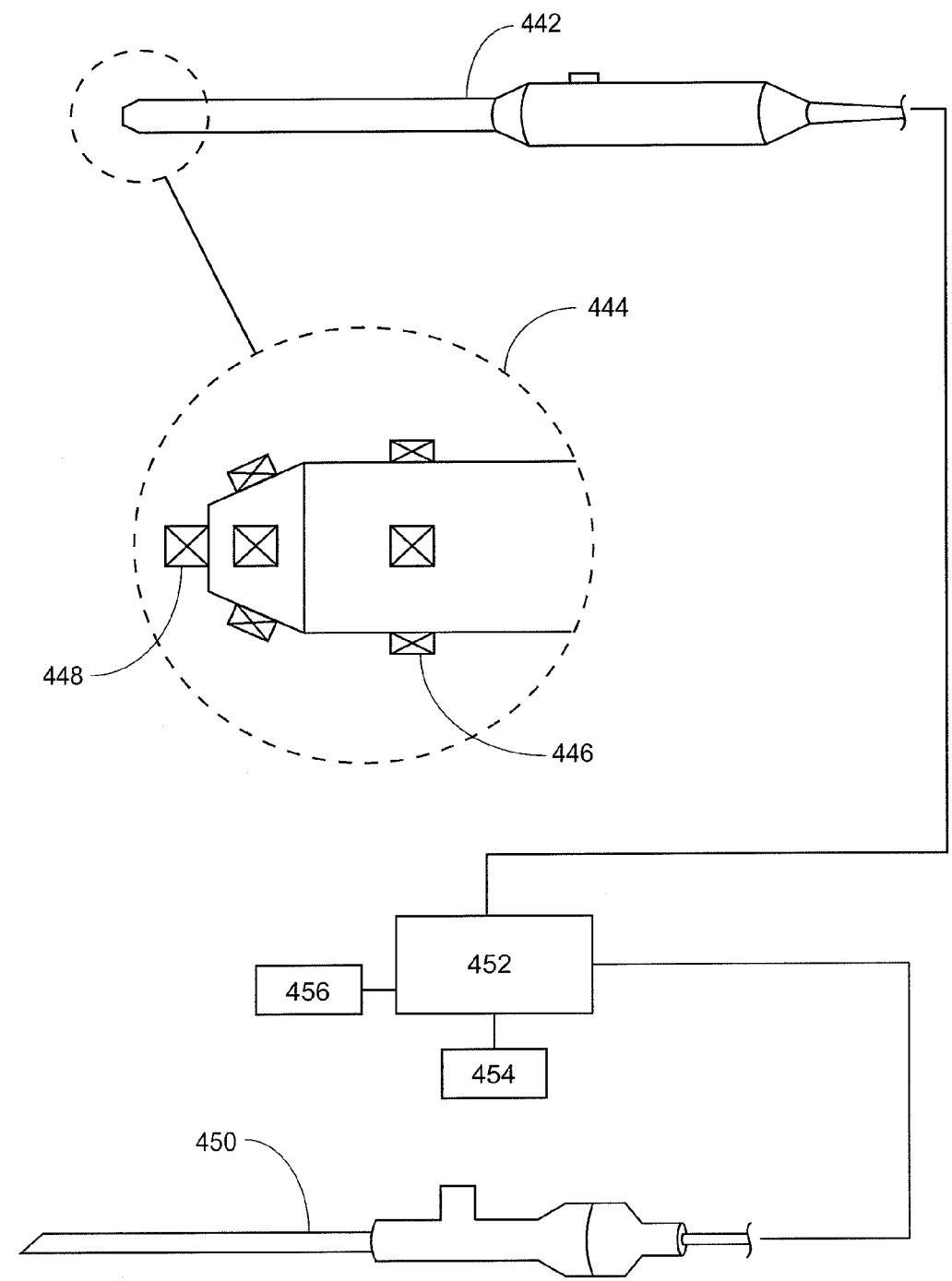
FIG. 4J is a schematic of an imaging system according to an embodiment.
Figure 5A:
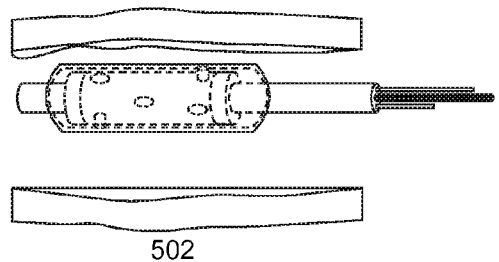
FIGS. 5A-5E illustrate a process for imaging using an imaging system in accordance with some embodiments.
Figure 5B:
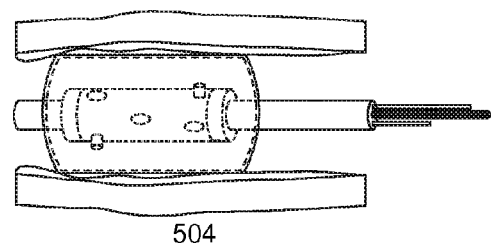
Figure 5C:
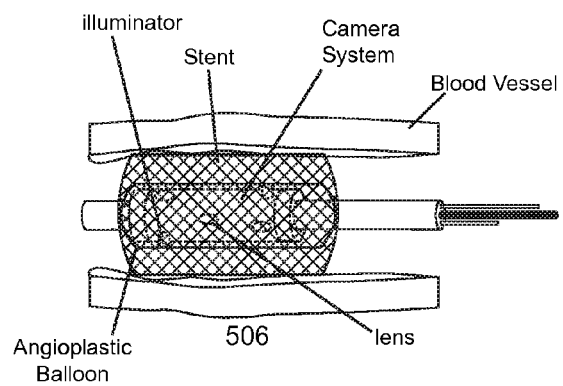
Figure 5D:
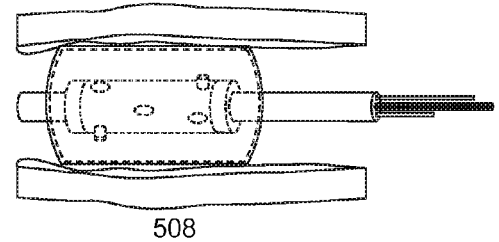
Figure 5E:
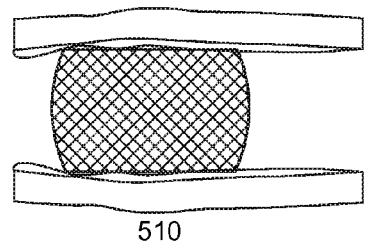

FIG. 4J illustrates a system 440 where an imaging device 442 is in the form of a probe that may be used in a laparoscopic procedure. The distal end 444 of the imaging device 442 is configured with an array of imaging sensors 446, which, for example, may take the form of any of the imaging sensors and sensors disclosed herein. In the case of an arthroscopic procedure, ultrasound imaging sensors may be used since the joint being operated on is typically filled with a flowing supply of saline. The imaging device 442 may optionally include a distal therapeutic apparatus 448, such an RF or mechanical ablation tip. A scope device 450 can be used in conjunction with the imaging device 442. The scope device 450 and imaging device 442 are both operatively coupled to a imaging system 452 having a processor, memory 454, and a display 456. The imaging system can be configured to process images that are simultaneously supplied by the scope device 450 and the imaging device 442.

Exemplary Uses:

FIGS. 5A through 5E illustrate a process for imaging using an imaging system in accordance with some embodiments. In the example shown, the imaging system includes a balloon covered camera system having three angularly and axially spaced lenses mounted on a catheter and inserted into an intravascular space. The imaging system further includes two illuminators configured to illuminate the interior of the balloon and project markings onto an interior surface of the balloon. The imaging system is applied to vascular stenting procedure. At operation 502, the un-deployed stent placed over the imaging system is inserted into the vascular space and placed at the stenting site. At operation 504, the balloon is inflated for the first time and stent is deployed. The rate at which the balloon is inflated and the pressure applied to the balloon should be sufficient to deploy the stent but not sufficient to damage the vascular structure. In some embodiments, a balloon (e.g., a second balloon attached to the catheter) can be used to characterize the stenting site prior to deploying the stent. The site can be characterized by for example the pressure it takes for the blood vessel at the stenting site to give way and stretch and by visually inspecting the stenting site using an imaging system. At operation 506, the balloon is deflated and the stent remains deployed and supports the vascular structure. At operation 508, the balloon is inflated for the second time to check whether the stent still remains in place. At operation 510, the balloon is withdrawn from the deployed stent after continuation of good placement in operation 508.

FIGS. 6A through 6F illustrate a process for imaging using an imaging system in accordance with some embodiments. In the example shown, the imaging system includes two balloon covered camera systems, each having three angularly and axially spaced lenses mounted on a catheter and inserted into an intravascular space. One balloon covered camera system is used for characterizing the valve before replacing it with an artificial valve with a second balloon covered camera system. Although two balloon covered camera systems are used here for characterizing the heart valve and for deploying an artificial replacement valve, a single balloon covered camera system may be used for characterizing the heart valve and for deploying an artificial replacement valve. In such cases, the replacement heart valve is slipped onto the balloon covered camera system after the valve has been characterized and prepped (e.g., removing calcium deposit and tissue flaps using laser). In some embodiments, the two balloon covered imaging systems each includes two illuminators configured to illuminate an interior of the balloon placed over it and project markings onto an interior surface of the balloon. The imaging system is applied to heart valve replacement.

Figure 6A:
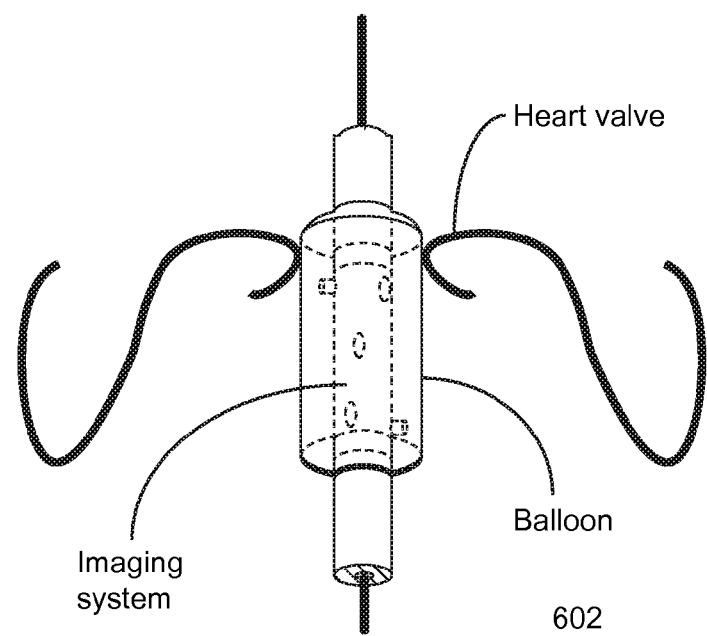
FIGS. 6A-6F illustrate a process for imaging using an imaging system in accordance with some embodiments.
Figure 6B:
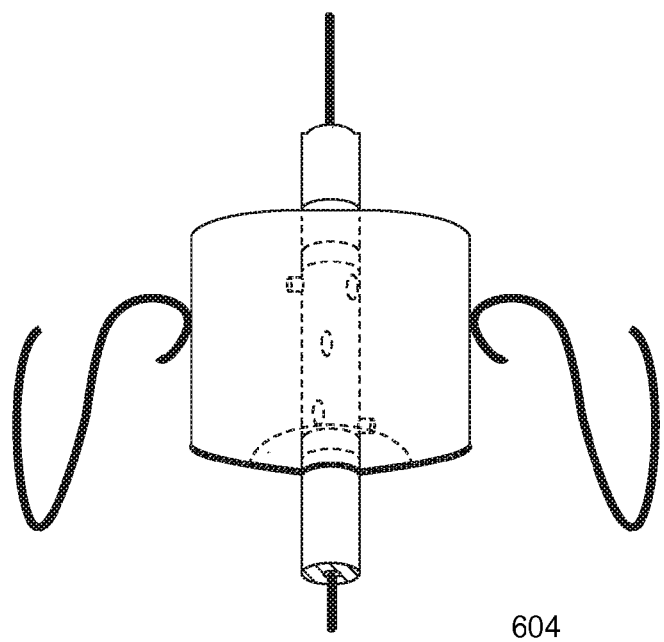
Figure 6C:
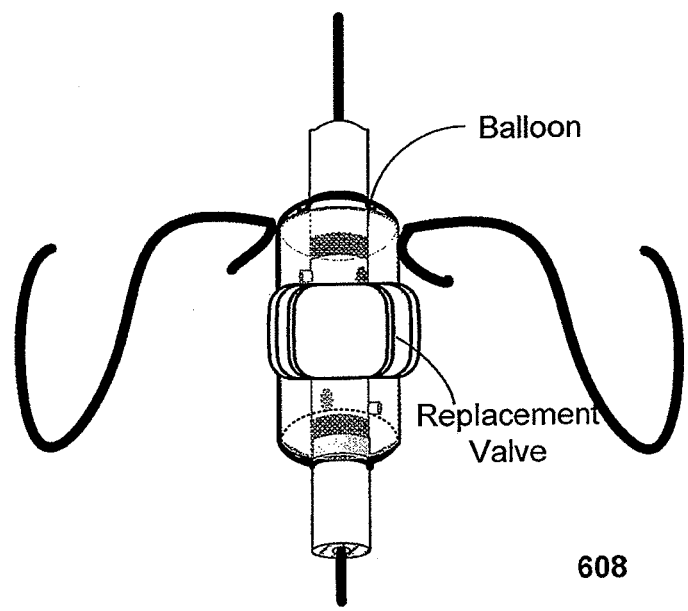
Figure 6D:
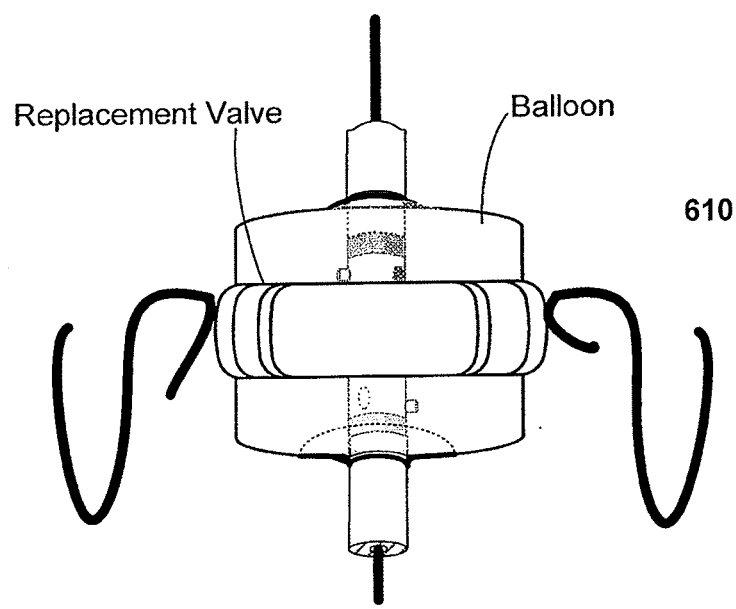
Figure 6E:
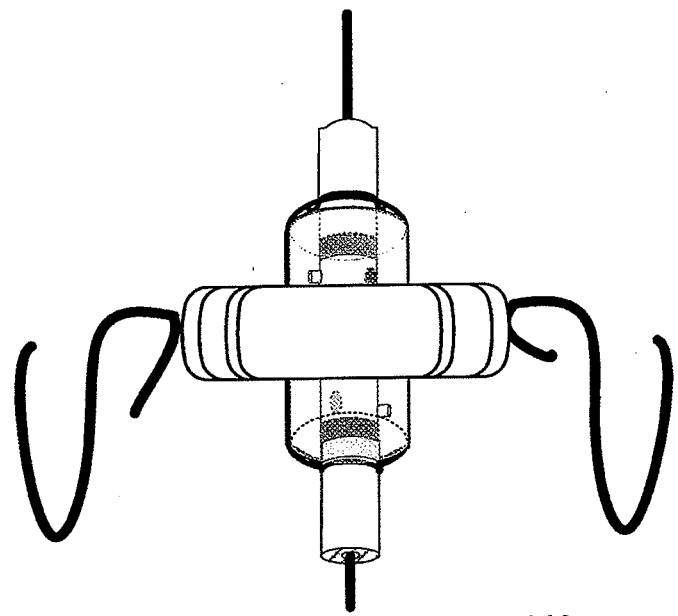
Figure 6F:
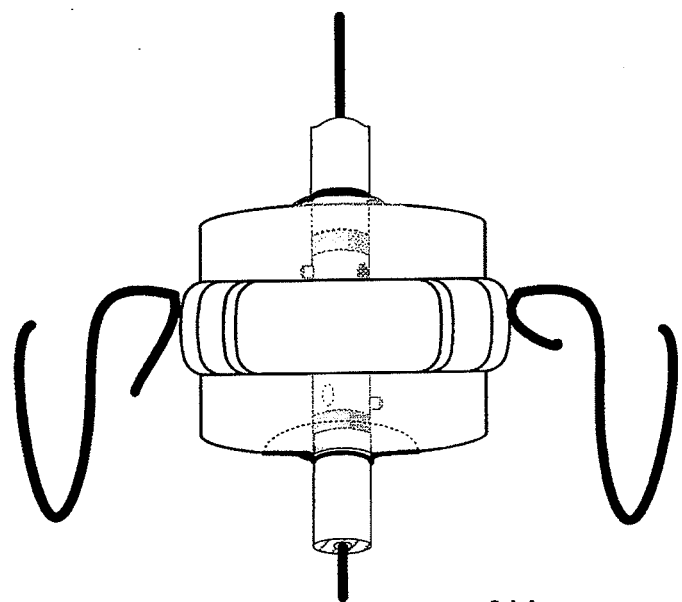

With reference to FIGS. 6A and 6B, at operation 602 a first balloon covered camera system is inserted into the heart valve. At operation 604, the first balloon is deployed to characterize the valve. The valve can be characterized by visually inspecting images of the balloon captured by the balloon covered imaging system as the balloon assumes the shape of the underlying features of the valve. The images are captured by the balloon covered imaging system, processed and rendered by a image processing device coupled to the first balloon covered imaging system using image processing and rendering algorithms. The valve can also be characterized by correlating the images of the balloon surface as it conforms to the underlying features of the valve at different balloon pressures. In some embodiments, the pressure in the balloon is monitored and images are captured for various pressures, thus providing a characterization of the subject surface as the outward force on the subject surface increases.

In some embodiments, for each pressure a new set of renderings (e.g., surface renderings, cross sections, 3D renderings, etc) may be made that show how the physical characteristics of portions of the subject surface change as a function of balloon force or pressure. For example, in some embodiments, multiple cross sections through the artery, valve, and/or ventricle may be rendered and characterized as a function of pressure. This information may be used in some embodiments to determine the diameter of the artery or valve as a function of outward force or balloon pressure, or may be used to determine if all portions of the artery or valve yield uniformly with force or pressure or if some portions yield more readily than others. For example a first bump of a first pliancy may deform at relatively low pressure to indicate soft masses, while a second bump of a second pliancy may deform, or not deform, at comparatively higher pressure to the first bump or with respect to an adjacent tissue wall or with respect to known information. This may indicate that the second bump is hard plaque or a calcium deposit that may need to be removed. Furthering this example, in some embodiments, multiple images can be taken over a varied range of pressures, where rates of relative deformation between the bodily aspects can be extrapolated to help determine tissue types. For example, the first bump may deform over a small low-pressure range, while the second burn may deform over a wide low to high-pressure range. Such information can be useful for interpretation of physical characteristics.

In some embodiments, the rendered 2-D or 3D properties of the various portions of the site as a function of balloon pressure or outward force may be used to determine if possible site preparation work is required in advance of insertion of the prosthetic valve, for example removal of plaque or calcium or partial removal of a portion of the valve. The rendered 2-D or 3D properties of the various portions of the site as a function of balloon pressure or outward force may be used in some embodiments to determine the best choice of physical properties for a prosthetic heart valve that best suits the site out of a predetermined set of available prosthetic heart valves. For example, the enhanced imaging embodiments disclosed herein can allow improved dimensional accuracy of the various cross sections of the site as a function of balloon pressure or outward force, thus leading to a better characterization of the best available final diameter of the installed prosthetic heart valve. As another example, if the artery, ventricle and/or valve present in the site yields in diameter at relatively low balloon pressure or force, then a prosthetic heart valve that has relatively low expansion force may be best suited, whereas if one or more of the components of the site require relatively high balloon pressure or force to yield to a given diameter then a prosthetic heart valve that has relatively high expansion force may be best suited.

With reference to FIGS. 6C-6F, at operation 608, a replacement heart valve is selected, placed over a second balloon covered imaging system, and inserted into valve opening. At operation 610, the replacement valve is deployed using a balloon inflation rate and pressure that are sufficient to deploy the artificial valve yet not sufficient to cause damages to the tissue at the valve replacement site. At operation 612, the second balloon is deflated while the replacement valve stays in place. At operation 614, the second balloon is deployed to check whether the stent has been successfully deployed and remains open. This can be done by examining the images captured, processed and rendered, and by examining the pressure it takes for the balloon to push open the valve.

Although the foregoing embodiments have been described in some detail for purposes of clarity of understanding, the invention is not limited to the details provided. There are many alternative ways of implementing the invention. The disclosed embodiments are illustrative and not restrictive.

Expandable Balloon Covering

In accordance with some embodiments, in some situations it may be desirable to precisely control the expansion of an expandable balloon, allowing it to expand in a desired direction while restricting expansion in an undesired direction. For example, angioplastic balloons are used to compress atherosclerotic plaque to open up the blood vessel and increase blood flow rate, it is thus desirable to focus the expansion in the radial direction so that maximum force can be exerted on the plaque. It may also desirable to minimize the expansion in the axial/longitudinal direction as it limits the balloon's ability to expand in the desired radial direction and reduces the force that can be exerted on the plaque. In addition, uncontrolled expansion in the undesired axial/longitudinal direction may cause damages to the surrounding tissues, particularly at a bend. Endothelial damage during angioplastic procedure is considered to be responsible for most of the re-stenosis in the treated arteries and for occasionally causing blood vessel occlusion when platelets, white blood cells and monocytes adhere to the damaged endothelial wall. Thus expandable balloon that can maximize expansion in the desired directions and minimize expansion in the undesired directions are needed.

In addition, in imaging or sensing applications where a camera, ultrasound, radio frequency, resistive measurement, or other sensing system is inserted into the balloon interior, in some embodiments, the balloon is inflated until it makes contact with the interior surface of an artery, vein, ventricle, heart valve, or other body space for the purposes such as imaging the surface of a subject (e.g., artery wall or heart valve inclusive of plaque, calcium deposits or other contaminants), cross section of a subject or other 3D or 2-D rendering of a subject. In such embodiments, it is desirable to limit axial expansion of the balloon so that the balloon expands principally in the radial dimension and to the greatest degree possible maintains a uniform outward force across the contact surface as a function of balloon pressure.

Accordingly, further disclosed herein are several methods and devices that may be applied to limit axial expansion of balloons for angioplasty, sensing or imaging applications. These methods and devices may provide several advantageous techniques and embodiments for improving the uniformity of pressure across a contact surface for angioplasty, sensing or imaging applications.

Figure 7A:
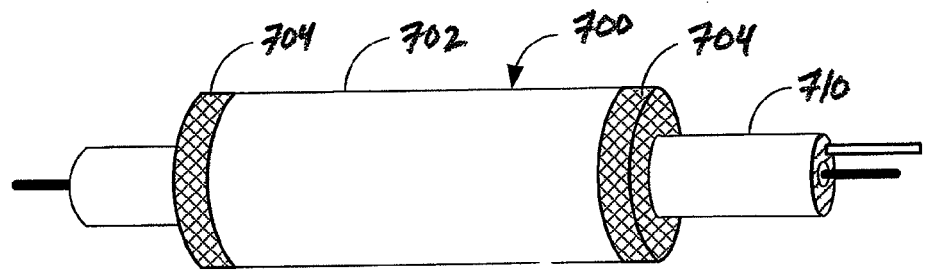
FIGS. 7A-7D are diagrams illustrating an expandable covering in accordance with some embodiments.
Figure 7B:
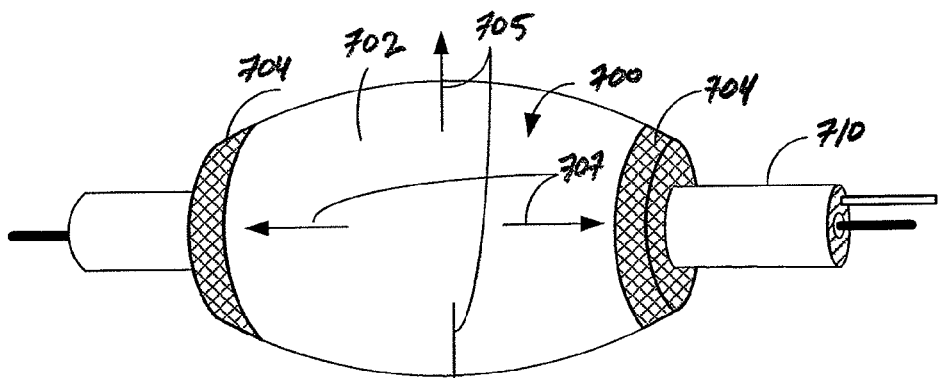
Figure 7C:
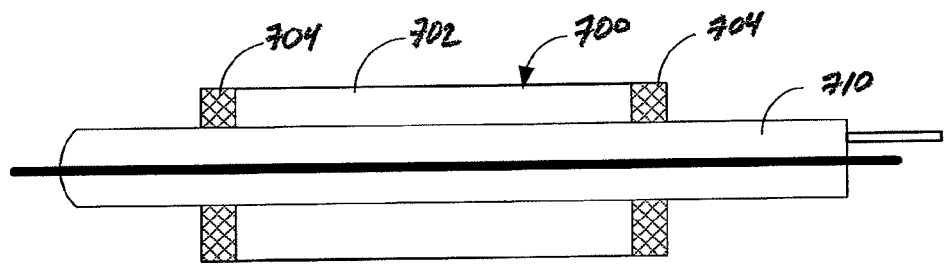
Figure 7D:
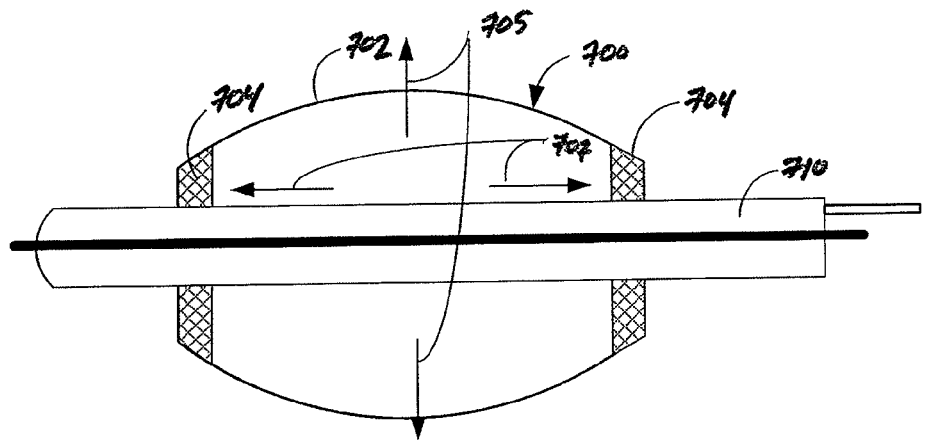

FIGS. 7A-7D are diagrams illustrating an expandable covering in accordance with various embodiments. As shown, an expandable covering 700 is provided, such as an expandable angioplastic balloon that limits axial/longitudinal expansion while maximizing expansion in the radio direction. FIG. 7A is a side view of the expandable covering 700 in a collapsed state. FIG. 7B is a side view of the expandable covering 700 in an expanded state. FIG. 7C is a cross section view of the expandable covering 700 in a collapsed state. FIG. 7D is a cross section view of the expandable covering 700 in an expanded state.

The expandable covering 700 includes a body having a first section 702 and a second section 704. The expandable covering 700 is mounted on a distal portion of a catheter 710. The balloon defines an inflatable chamber that is in fluid communication with a pressurizable fluid reservoir (not shown) for storing a fluid (e.g., air or sterile saline solution). An influx of the fluid to the inflatable chamber causes the body of the balloon to expand. An efflux of the fluid from the inflatable chamber causes the body of the balloon to contract. Expansion of the first section 702 causes the balloon 706 to expand in a first direction 705, in this case the radial direction 706, and expansion of the second section 702 causes the balloon to expand in a second direction 707, in this example the axial/longitudinal direction. The first section 702 expands relatively more freely than the second section 704, so when the balloon expands, it preferentially expands in the first direction 705.

In some embodiments, the first section 702 includes a thinner elastic material and the second section 704 includes a thicker version of the same elastic material. The first section 702 expands more freely than the second section 702 since it is thinner and it takes less force to expand compared to the second section 704. Thus when the balloon is inflated under pressure, it will preferentially expand in the first direction than the second direction.

In some embodiments, the first section 704 includes a first material and the second section 106 includes a second material, where the first material is more elastic than the second material and expands more freely than the second material. Thus when the balloon 706 is inflated under pressure, it will preferentially expand in the first direction than the second direction.

The covering 700 can be applied to any of the balloon using systems disclosed herein. In some embodiments, involving imaging or sensing apparatus inserted into a balloon, it is desirable to recognize that the balloon should be in intimate contact with the subject surface in order to obtain a good quality image of the subject by displaying or image processing an image that is taken of the interior of the balloon surface. For example, if the balloon expands in a non-uniform manner along the axial dimension, the center of the balloon axial dimension may expand more than the edges and therefore the center of the balloon may make intimate or reasonably uniform contact with the subject surface (e.g., interior of an artery, heart valve, ventricle, vein, or other body space), but the edges of the balloon axial dimension may not make contact in an intimate or reasonably uniform manner (e.g., possibly not making contact at all in some portions of the axial dimension).

In other balloon construction embodiments or application scenarios it may be that portions other than the center of the balloon axial dimension make good intimate and reasonably uniform contact with the subject surface while the center of the axial dimension may or may not make intimate or reasonably uniform contact. In such cases if the image captured on the inside of the balloon in the areas where the balloon is not in intimate or reasonably uniform contact with the subject surface then these portions of the image can provide erroneous information since these portions of the image can reflects mainly the balloon interior surface and not the subject surface.

In some embodiments, erroneous image information is removed or reduced by identifying the portions of the balloon that are in intimate or relatively uniform contact with the subject surface and using only the image information captured from those portions of the balloon surface. In one example embodiment, this is accomplished by primarily using the image information sensed from the interior portion of the axial dimension of the balloon or by ignoring or not capturing the image information sensed from part of the end portions of the balloon. In another embodiment, this is accomplished by identifying one or more portions of the balloon that are in intimate or reasonably uniform contact with the subject surface and primarily using the image information sensed from those portions of the balloon. In some embodiments, the interior of the balloon surface may be marked to indicate which portions of the balloon should be in intimate or reasonably uniform contact with the subject surface.

Although the foregoing embodiments have been described in some detail for purposes of clarity of understanding, the invention is not limited to the details provided. Further, the use of "X or more", X being an amount of aspects, should be understood to be interchangeable with the terms "at least X", as well as a "plurality" that is inherently greater than X. There are many alternative ways of implementing the invention. The disclosed embodiments are illustrative and not restrictive.

What is claimed is:

1. A method comprising:
    imaging a first cavity portion of a greater body cavity using at least one imaging sensor of a catheter to generate a first digital image;
    imaging a second cavity portion of the greater body cavity using the at least one imaging sensor of the catheter to generate a second digital image, wherein the first and second cavity portions are contiguous portions of the greater body cavity, and wherein first and second digital images partially overlap in an overlap portion;
    generating a greater image parameter of the greater body cavity from at least the first and second digital images, the generating including identifying the overlap portion in the first image, identifying the overlap portion in the second image, and using the identified overlap portion to combine the first and second images to generate the greater image parameter,
    wherein combining the first and second images to generate the greater image parameter includes performing an image combining operation comprising:
        applying a first correction factor, first scaling factor, or first calibration factor to at least part of the first digital image to create a corrected first digital image, and
        combining information from the corrected first digital image and the second digital image to form the greater image parameter; and
    generating a greater image from at least the corrected first digital image, second digital image and greater image parameter.

2. The method of claim 1, wherein generating the greater image parameter comprises applying an algorithm that identifies common features of each of the first and second images in the overlap portion and adjusting at least one of the first and second images according to the common features.

3. The method of claim 2, wherein the first and second digital images are pixilated and wherein the common features comprise pixels features.

4. The method of claim 1, wherein a position of the catheter in the body cavity is maintained when imaging the first and second cavity portions.

5. The method of claim 1, wherein imaging the first cavity portion and imaging the second cavity portion are substantially simultaneous.

6. The method of claim 1, wherein the image combining operation further comprises applying an algorithm to minimize a measure of image error between two or more component images of the greater image or applying an algorithm to achieve a best fit between two or more component images of the greater image.

7. The method of claim 1, wherein the image combining operation further comprises applying an algorithm to minimize a measure of image error for an image calibration aspect or applying an algorithm to achieve a best fit with an image calibration aspect.

8. The method of claim 1, wherein the at least one imaging sensor comprises a plurality of imaging sensors that are angularly separated on a circumference of the catheter.

9. The method of claim 1, wherein the at least one imaging sensor comprises a plurality of imaging sensors that are axially separated on a circumference of the catheter.

10. The method of claim 1, wherein the at least one imaging sensor comprises a plurality of imaging sensors that are angularly and axially separated on a circumference of the catheter.

11. The method of claim 1, wherein the at least one imaging sensor comprises a plurality of imaging sensors, wherein the first digital image is generated from a first imaging sensor of the plurality of imaging sensors and the second digital image is generated from a second imaging sensor of the plurality of imaging sensors, and
    wherein the method further comprises inserting the catheter into an imaging subject having one or more calibration references each with a known imaging property or physical property, each of the first and second imaging sensors capturing in its field of view at least one of the one or more calibration references, and capturing images of at least one of the calibration references from the first and second imaging sensors.

12. The method of claim 11, wherein the imaging subject is a calibration assembly, wherein the method further comprises performing a calibration procedure prior to imaging the body cavity, the calibration procedure utilizing the known imaging property or physical property of at least one of the one or more calibration references and at least the first captured image to assist in determining the first correction factor, first scaling factor, or first calibration factor.

13. The method of claim 1, wherein the at least one imaging sensor comprises a plurality of imaging sensors, wherein the first digital image is generated from a first imaging sensor of the plurality of imaging sensors and the second digital image is generated from a second imaging sensor of the plurality of imaging sensors,
    wherein the method further comprises one or more calibration references being present in the body cavity, and wherein the first correction factor, first scaling factor, or first calibration factor is determined by identifying a known physical aspect or a known imaging aspect of the calibration reference while imaging the body cavity.

14. The method of claim 1, wherein the at least one imaging sensor comprises a plurality of imaging sensors, wherein the first digital image is generated from a first imaging sensor of the plurality of imaging sensors and the second digital image is generated from a second imaging sensor of the plurality of imaging sensors,
    wherein the method further comprises identifying one or more physical features or imaging features in the overlap portion that are common to both the first and second digital images, and wherein the first correction factor, first scaling factor, or first calibration factor is determined at least in part by comparing a portion of the first digital image that captures the one or more physical features or imaging features with a portion of the second digital image that captures the one or more physical features or imaging features.

15. The method of claim 1, wherein the at least one imaging sensor comprises a plurality of imaging sensors, wherein the first digital image is generated from a first imaging sensor of the plurality of imaging sensors and the second digital image is generated from a second imaging sensor of the plurality of imaging sensors, wherein the method further comprises inserting the catheter into an imaging subject having one or more calibration references, and encompassing the catheter in a sealed catheter balloon that is capable of being filled with fluid, wherein the first correction factor, first scaling factor, or first calibration factor is determined in part from a parameter of the calibration reference, and wherein the parameter of the calibration reference comprises a physical feature, a visible feature or material composition feature of the balloon.

16. The method of claim 1, wherein the at least one imaging sensor comprises a plurality of imaging sensors, wherein the first digital image is generated from a first imaging sensor of the plurality of imaging sensors and the second digital image is generated from a second imaging sensor of the plurality of imaging sensors, and wherein the common image aspect comprises a feature of the body cavity.

17. The method of claim 1, wherein the at least one imaging sensor generates an image utilizing visible light.

18. The method of claim 1, wherein the at least one imaging sensor generates an image utilizing non-visible light.

19. The method of claim 1, wherein the at least one imaging sensor generates an image utilizing laser light.

20. The method of claim 1, wherein the at least one imaging sensor generates an image utilizing ultrasound energy.

21. The method of claim 1, wherein the at least one imaging sensor generates an image utilizing radio frequency energy.

22. The method of claim 1, wherein the method further comprises encompassing the catheter in a sealed catheter balloon that is capable of being filled with fluid, wherein the balloon is pressurized with a multitude of fluid pressures within a portion of the body cavity having a pliancy, wherein a first image capture of the greater image parameter of the body cavity is generated when a first fluid pressure is present to cause a first deformation of balloon in the portion of the body cavity, and a second image capture of the greater image parameter of the body cavity is generated when a second fluid pressure is present to cause a second deformation of the balloon in the portion of the body cavity, and wherein the first image capture and the second image capture are then analyzed to determine at least one of the first deformation, the second deformation, the difference between the first and second deformations, or a measure of the compliancy.

23. The method of claim 1, wherein the method further comprises encompassing the catheter in a sealed catheter balloon that is capable of being filled with fluid, and wherein the balloon has an expandable covering that promotes expansion of the balloon in a radial dimension and restricts expansion in an axial direction.

24. The method of claim 1, wherein the at least one imaging sensor comprises a plurality of imaging sensors, encompassing the catheter in a sealed catheter balloon that is capable of being filled with fluid, and wherein the balloon has a plurality of balloon imaging references with at least one imaging reference being captured in the overlap portion.

25. The method of claim 24, wherein the plurality of balloon imaging references comprise distortable reference markings, and wherein a measure of distortion of the distortable reference markings is utilized to determine a physical property of the greater image parameter.

26. The method of claim 1, wherein the method further comprises encompassing the catheter in a sealed catheter balloon that is capable of being filled with fluid, wherein pressurization of the balloon is utilized to install a stent.

27. The method of claim 26, wherein the greater image parameter is utilized to determine an effectiveness of the stent installation.

28. The method of claim 1, wherein the greater image parameter comprises a 2-D image of a portion of the body cavity.

29. The method of claim 1, wherein the greater image parameter comprises a 3-D surface image of a portion of the body cavity.

30. The method of claim 1, wherein the greater image parameter comprises a 3-D rendering of a portion of the body cavity.

31. The method of claim 1, wherein the greater image parameter comprises a cross-section of a portion of the body cavity.

32. The method of claim 1, wherein the greater image parameter comprises a diameter of a portion of the body cavity.

33. The method of claim 1, wherein the greater image parameter comprises a dimension of the body cavity.

34. The apparatus of claim 1, wherein the catheter includes a stent proximate to a balloon.

35. The apparatus of claim 1, wherein the at least one imaging sensor comprises a single imaging sensor that is configured to rotate within the body cavity, and wherein the first digital image and second digital image are generated at differing rotational angles.

36. The method of claim 1, wherein the first correction factor, first scaling factor, or first calibration factor adjusts for relative image scaling between the portion of the first digital image and the portion of the second digital image.

37. The method of claim 1, wherein the first correction factor, first scaling factor, or first calibration factor adjusts for a relative image view angle or imaging angle between the portion of the first digital image and the portion of the second digital image.

38. The method of claim 1, wherein the first correction factor, first scaling factor, or first calibration factor adjusts for a relative image pixel location or pixel angle between the portion of the first digital image and the portion of the second digital image.

39. The method of claim 1, wherein the first correction factor, first scaling factor, or first calibration factor adjusts for a relative image sensor distortion between the portion of the first digital image and the portion of the second digital image.

40. The method of claim 1, wherein the first correction factor, first scaling factor, or first calibration factor adjusts for a relative lens or optical fiber distortion between the portion of the first digital image and the portion of the second digital image.

41. The method of claim 1, wherein the first correction factor, first scaling factor, or first calibration factor adjusts for a relative image capture position between the portion of the first digital image and the portion of the second digital image.

42. The method of claim 1, wherein the first correction factor, first scaling factor, or first calibration factor adjusts for a relative image beam angle or array scan angle between the portion of the first digital image and the portion of the second digital image.

43. The method of claim 1, wherein the first correction factor, first scaling factor, or first calibration factor adjusts for a relative sensor position between the portion of the first digital image and the portion of the second digital image.

44. The method of claim 1, wherein the first correction factor, first scaling factor, or first calibration factor adjusts for a relative image calibration between the portion of the first digital image and the portion of the second digital image.

45. The method of claim 1, wherein the at least one imaging sensor comprises a plurality of imaging sensors, and wherein the first digital image contains information derived from a first subset of the plurality of imaging sensors containing at least one sensor that is not contained in the second subset of the plurality of imaging sensors.

46. The method of claim 1, wherein the first digital image contains information derived from the at least one imaging sensor when it is located in a first position and the second digital image contains information derived from the at least one image sensor when it is located in a second position.

47. The method of claim 1, wherein the at least one imaging sensor comprises at least one ultrasound transducer.

48. The method of claim 1, wherein the at least one imaging sensor comprises at least one ultrasound transducer, and wherein the method further comprises locating the at least one ultrasound transducer on the catheter.

49. The method of claim 1, wherein the at least one imaging sensor comprises at least one ultrasound transducer, and wherein the method further comprises encompassing the catheter in a sealed catheter balloon that is capable of being filled with fluid.

50. The method of claim 49, wherein the balloon has a plurality of balloon imaging references in the fields of view of the at least one ultrasound transducer.

51. The method of claim 1, wherein the at least one imaging sensor comprises at least one array of ultrasound transducers.

52. The method of claim 1, wherein the at least one imaging sensor comprises a plurality of ultrasound transducer arrays.

53. The method of claim 1, wherein the at least one imaging sensor comprises at least one radio frequency transducer.

54. The method of claim 1, wherein the at least one imaging sensor comprises at least one radio frequency transducer, and wherein the method further comprises locating the at least one radio frequency transducer on the catheter.

55. The method of claim 1, wherein the at least one imaging sensor comprises at least one radio frequency transducer, and wherein the method further comprises encompassing the catheter in a sealed catheter balloon that is capable of being filled with fluid.

56. The method of claim 55, wherein the balloon has a plurality of balloon imaging references in the fields of view of the at least one radio frequency transducer.

57. The method of claim 1, wherein the at least one imaging sensor comprises at least one array of radio frequency transducers.

58. The method of claim 1, wherein the at least one imaging sensor comprises a plurality of radio frequency transducer arrays.

59. The method of claim 1, wherein the at least one imaging sensor comprises one of: an optical sensor, a charge coupled device, an active pixel sensor, a lens, an optical fiber or a combination thereof.

60. The method of claim 1, wherein the at least one imaging sensor comprises at least one optical sensor, lens, or optical fiber, and wherein the method further comprises locating the at least one optical sensor, lens, or optical fiber on the catheter.

61. The method of claim 1, wherein the at least one imaging sensor comprises at least one optical sensor, lens, or optical fiber, and wherein the method further comprises encompassing the optical sensor, lens, or optical fiber in a sealed catheter balloon that is capable of being filled with fluid.

62. The method of claim 61, wherein the balloon has a plurality of balloon imaging references in the fields of view of the at least one optical sensor.

63. The method of claim 1, wherein the at least one imaging sensor comprises a multitude of optical sensors, lenses, or optical fibers.

64. The method of claim 1, wherein the at least one imaging sensor comprises at least one signal transducer capable of transmitting a signal and measuring a return time or distance for one or more signal reflections.

65. The method of claim 1, wherein the at least one imaging sensor comprises a multitude of signal transducers, each capable of measuring a return time or distance for one or more signal reflections.

66. A method comprising:
   imaging a first cavity portion of a greater body cavity using at least one imaging sensor of a catheter to generate a first digital image;
   imaging a second cavity portion of the greater body cavity using the at least one imaging sensor of the catheter to generate a second digital image, wherein the first and second cavity portions are contiguous portions of the greater body cavity, and wherein first and second digital images partially overlap in an overlap portion;
   generating a greater image parameter of the greater body cavity from at least the first and second digital images, the generating including identifying the overlap portion in the first image, identifying the overlap portion in the second image, and using the identified overlap portion to combine the first and second images to generate the greater image parameter,
   wherein combining the first and second images to generate the greater image parameter includes performing an image combining operation comprising:
      applying a first correction factor, first scaling factor, or first calibration factor to at least part of the first digital image to create a corrected first digital image,
      applying a second correction factor, second scaling factor, or second calibration factor to at least part of the second digital image, and
      combining information from the corrected first digital image and the corrected second digital image to form the greater image parameter; and
   generating a greater image from at least the corrected first digital image, corrected second digital image, and greater image parameter.

* * * * *